United States Patent [19]
Thorne et al.

[11] Patent Number: 5,836,917
[45] Date of Patent: *Nov. 17, 1998

[54] SELF RETRACTING MEDICAL NEEDLE APPARATUS AND METHODS

[75] Inventors: David L. Thorne, Kaysville; Gale H. Thorne, Bountiful, both of Utah

[73] Assignee: Specialized Health Products, Inc., Bountiful, Utah

[*] Notice: The term of this patent shall not extend beyond the expiration date of Pat. No. 5,480,385.

[21] Appl. No.: 744,108

[22] Filed: Nov. 5, 1996

Related U.S. Application Data

[63] Continuation-in-part of Ser. No. 565,881, Dec. 1, 1995, Pat. No. 5,616,135, which is a continuation-in-part of Ser. No. 455,514, May 31, 1995, Pat. No. 5,549,708, and a continuation of Ser. No. 370,728, Jan. 10, 1995, Pat. No. 5,480,385, and a continuation-in-part of Ser. No. 436,976, May 8, 1995, Pat. No. 5,487,794, and a continuation-in-part of Ser. No. 484,533, Jun. 7, 1995, Pat. No. 5,542,927, which is a continuation-in-part of Ser. No. 370,728, Jan. 10, 1995, Pat. No. 5,480,385.

[51] Int. Cl.⁶ .................................................. A61M 5/00
[52] U.S. Cl. .................................... 604/164; 604/263
[58] Field of Search .............................. 604/195, 198, 604/192, 187, 263, 110, 264, 164, 158, 165, 171

[56] References Cited

U.S. PATENT DOCUMENTS

| | | | |
|---|---|---|---|
| 3,587,575 | 6/1971 | Lichenstein | 128/128 |
| 4,676,783 | 6/1987 | Jagger | 604/171 |

(List continued on next page.)

FOREIGN PATENT DOCUMENTS 9-28811  2/1997  Japan.

OTHER PUBLICATIONS

Patricia Seremet, "Small Tolland Company Takes Jab at Safety Needle Market," *The Hartford Courant*, Sep. 13, 1995, pp.: F1 and F3.

*Primary Examiner*—John D. Yasko
*Attorney, Agent, or Firm*—Gale H. Thorne

[57] ABSTRACT

Method and apparatus associated with safe retraction of medical needles after use. Embodiments are disclosed for combinations comprising medical syringes and self-retracting needle systems. An energy-storing, needle-retracting mechanism comprises an elastic tubing which also is taught perform a plurality of functions comprising the storing of force by which a medical needle is retracted, slidable seals, normally dosed valves and dynamic volume control by which fluid regurgitation upon needle retraction is voided. Selective, constrictive control of the internal volume of the tubing when stretched effectively inhibits regurgitant flow from the needle as the tubing relaxes while retracting the needle. In all embodiments, needle retraction is initiated by forces applied in a direction transverse to the long axis of the needle using but a single hand. The syringe may be used in a plurality of modes such as a standard syringe or as a pre-filled syringe. Methods for making and assembling the combination are also disclosed. Invention manufacture requires only a minimal number and complexity of parts such that a projected manufacturing cost is potentially low enough to permit the apparatus to be cost competitive with contemporary combinations of hypodermic syringes and non-self retracting needle systems.

3 Claims, 30 Drawing Sheets

U.S. PATENT DOCUMENTS

| | | | |
|---|---|---|---|
| 4,747,831 | 5/1988 | Kulli | 604/110 |
| 4,813,936 | 3/1989 | Schroeder | 604/195 |
| 4,828,548 | 5/1989 | Walter | 604/164 |
| 4,850,374 | 7/1989 | Diaz-Ramos | 128/763 |
| 4,892,525 | 1/1990 | Hermann, Jr. | 604/263 |
| 4,909,794 | 3/1990 | Haber | 604/195 |
| 4,936,830 | 6/1990 | Verlier | 604/110 |
| 4,946,446 | 8/1990 | Vadher | 604/198 |
| 4,955,870 | 9/1990 | Ridderheim | 604/195 |
| 4,966,593 | 10/1990 | Lennox | 604/198 |
| 4,978,340 | 12/1990 | Terrill | 604/195 |
| 4,985,021 | 1/1991 | Straw | 604/198 |
| 4,986,816 | 1/1991 | Steiner | 604/192 |
| 4,988,339 | 1/1991 | Vadher | 604/197 |
| 4,994,034 | 2/1991 | Botich | 604/110 |
| 4,995,870 | 2/1991 | Baskas | 604/110 |
| 5,092,853 | 3/1992 | Couvertier | 604/195 |
| 5,098,402 | 3/1992 | Davis | 604/195 |
| 5,114,404 | 5/1992 | Paxton | 604/110 |
| 5,147,303 | 9/1992 | Martin | 604/110 |
| 5,180,370 | 1/1993 | Gillespie | 604/110 |
| 5,188,599 | 2/1993 | Botich | 604/110 |
| 5,193,552 | 3/1993 | Columbus et al. | 128/760 |
| 5,195,983 | 3/1993 | Boese | 604/192 |
| 5,195,985 | 3/1993 | Hall | 604/195 |
| 5,205,823 | 4/1993 | Zdeb | 604/110 |
| 5,205,824 | 4/1993 | Mazur | 604/110 |
| 5,209,739 | 5/1993 | Talslay | 604/195 |
| 5,215,533 | 6/1993 | Robb | 604/195 |
| 5,246,428 | 9/1993 | Falknor | 604/198 |
| 5,254,099 | 10/1993 | Kuracina | 604/198 |
| 5,256,153 | 10/1993 | Hake | 604/198 |
| 5,267,976 | 12/1993 | Guerineau | 604/198 |
| 5,320,606 | 6/1994 | Jore | 604/110 |
| 5,356,392 | 10/1994 | Firth et al. | 604/198 |
| 5,374,250 | 12/1994 | Dixon | 604/110 |
| 5,573,510 | 11/1996 | Issacson | 640/158 |

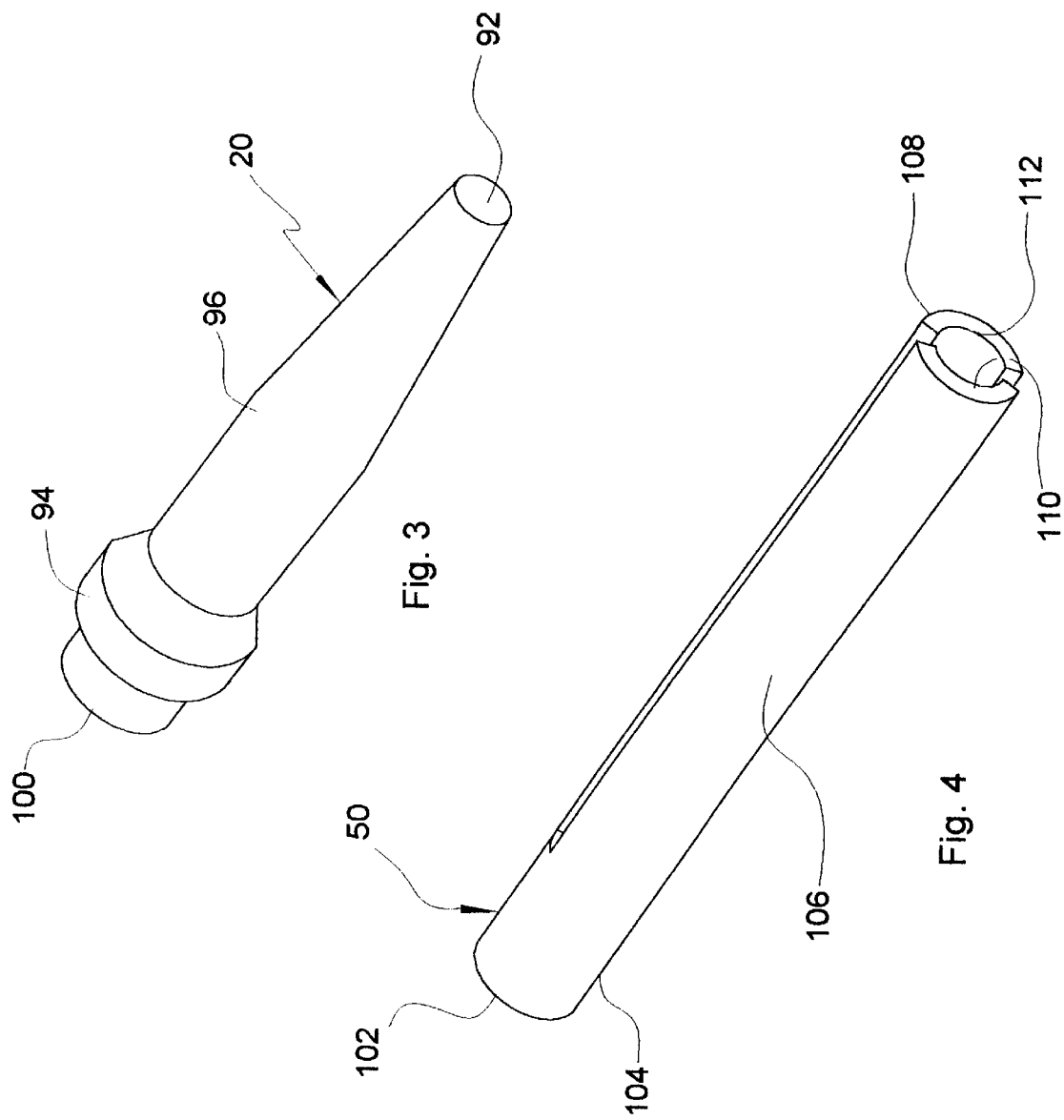

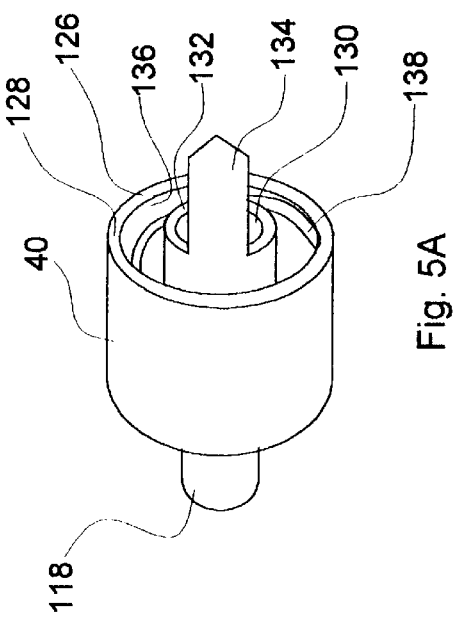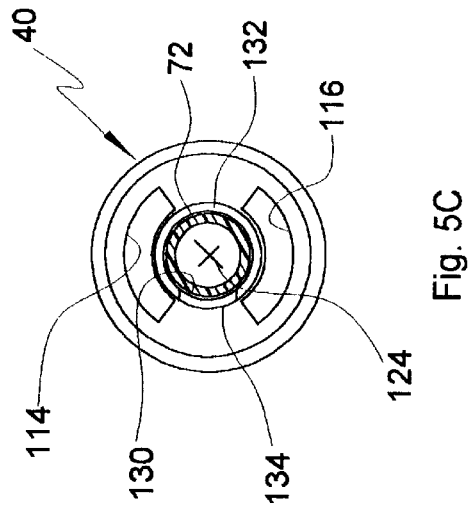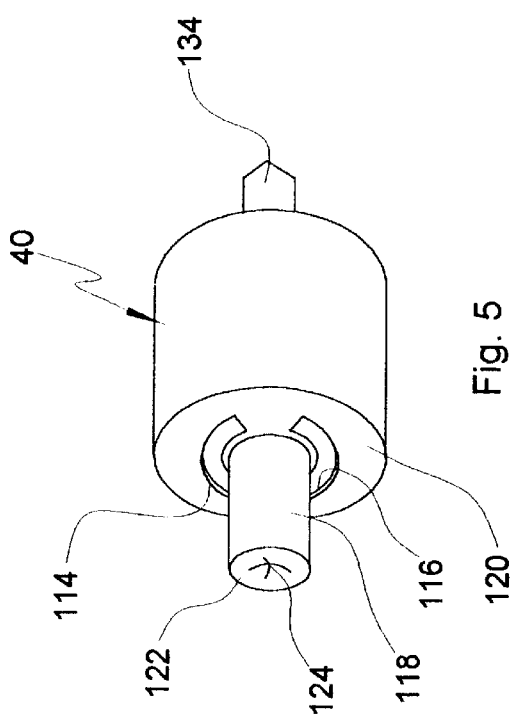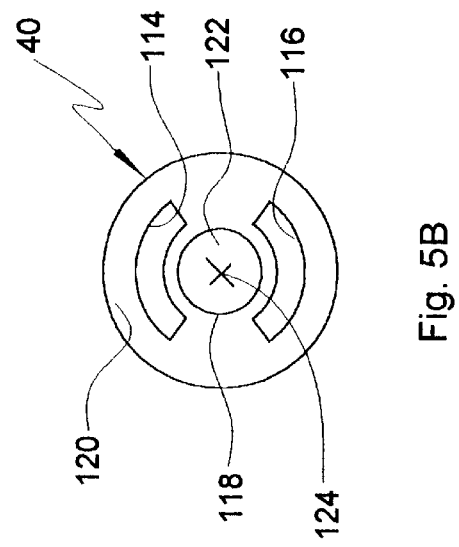

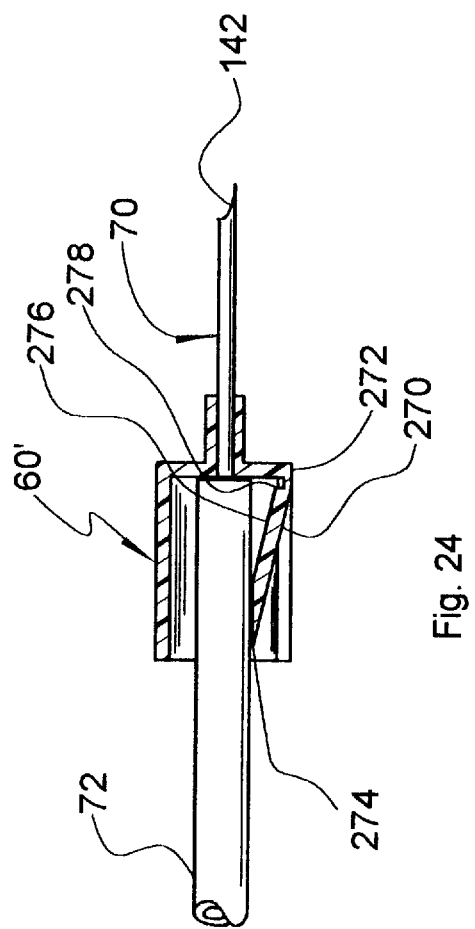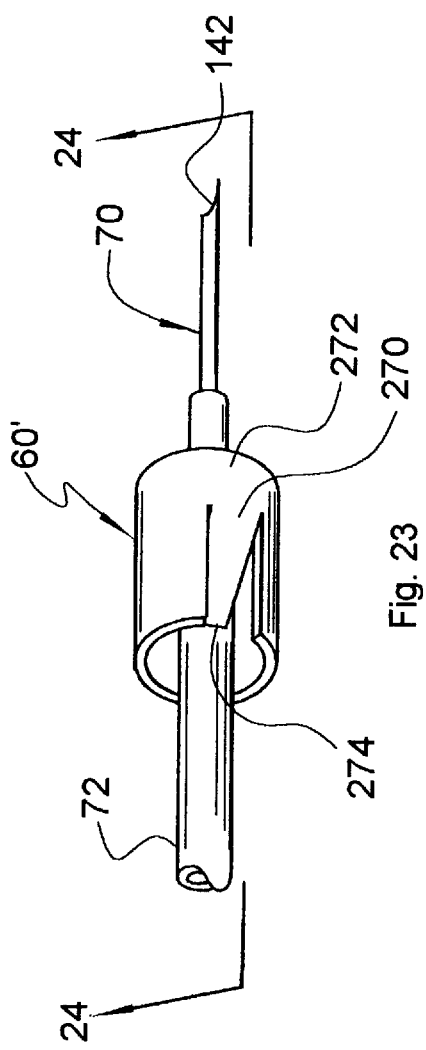

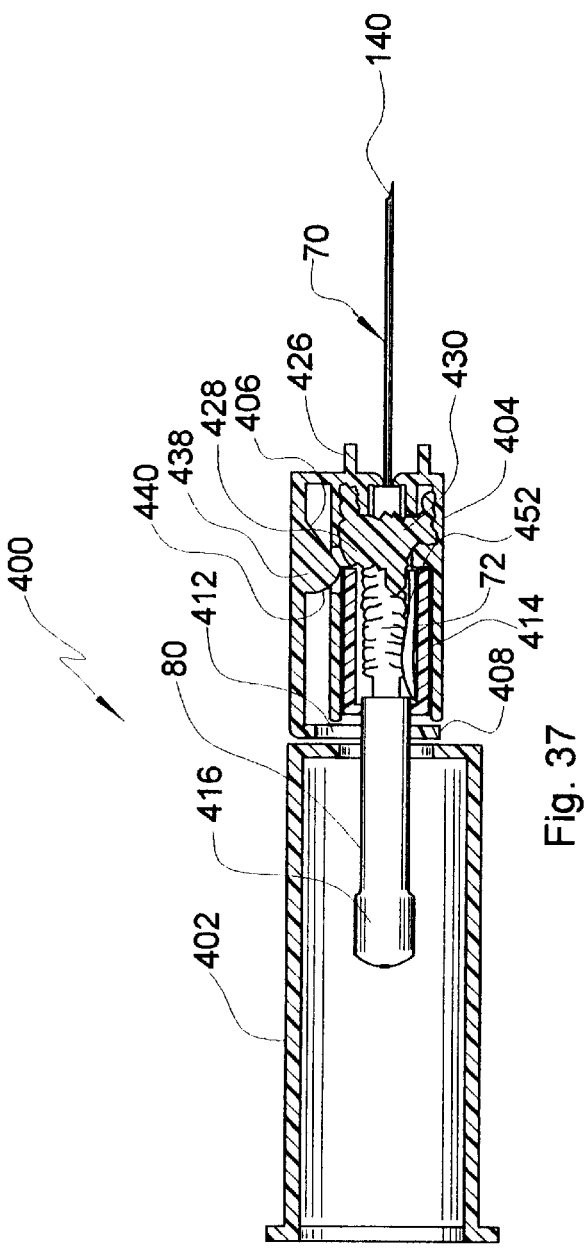
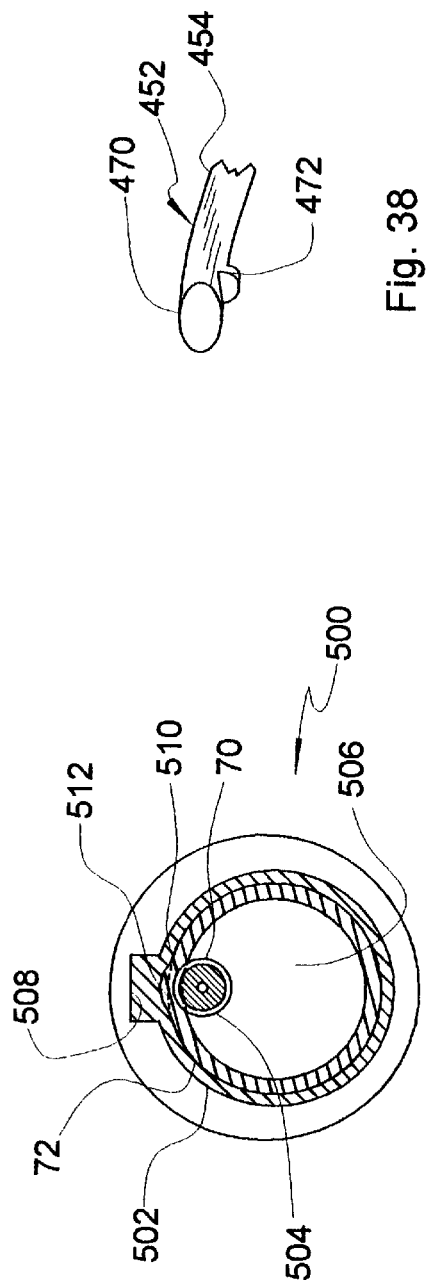
Fig. 37
Fig. 38
Fig. 39

SELF RETRACTING MEDICAL NEEDLE APPARATUS AND METHODS

CONTINUATION

This application for patent is a continuation-in-part of U.S. patent application Ser. No. 08/565,881 filed Dec. 1, 1995, now U.S. Pat. No. 5,616,135, which is a continuation-in-part of U.S. Pat. No. 5,549,708 (application Ser. No. 08/455,514 filed May 31, 1995), a continuation of U.S. Pat. No. 5,480,385 (application Ser. No. 08/370,728 filed Jan. 10, 1995) and also a continuation-in-part of U.S. Pat. No. 5,487,734 (application Ser. No. 08/436,976 filed May 8, 1995) and U.S. Pat. No. 5,542,927 (application Ser. No. 08/484,533 filed Jun. 7, 1995) which are continuations-in-part of Ser. No. 370,728 U.S. Pat. No. 5,480,385, the disclosures of which are specifically incorporated hereby reference.

FIELD OF INVENTION

This invention relates generally to medical needle apparatus and methods and particularly to apparatus comprising medical needles which are self-retracting from an extended position at which the needle is used to a retracted position where the needle is fully withdrawn and encased within a housing for safe disposal. Further, the invention is related to medical products which may only be used once to eliminate cross contamination from one patient to another and to those medical products which have sterile parts inherently protected from contamination without need of additional packaging apparatus.

PRIOR ART

Problems associated with inadvertent needle sticks are well known in the art of blood withdrawal, transdermal medication injection, catheter emplacement and other medical procedures involving uses of medical needles. Ever increasing attention is being paid to needle stick problems due to the contemporary likelihood of being exposed to AIDS and Hepatitis.

Commonly, procedures involving needle withdrawal require a technician to use one hand to place pressure at the wound site where a needle is being withdrawn while removing the needle apparatus with the other hand. It is common practice for an attending technician to give higher priority to care for the wound than is given to disposal of a needle. Such priority either requires an available sharps container within ready reach or another means for safe disposal without leaving the patient's side. Providing adequate care is often compounded by patient condition and mental state (e.g. in burn units and psychiatric wards). Under such conditions, it is often difficult, if not impossible, to use appropriate procedures to properly dispose of a used, exposed needle while caring for a patient.

Widespread knowledge and history associated with needle care and disposal problems have resulted in conception and disclosure of a large number of devices, each of which represents an attempt to provide not only a solution to the problem of needle sticks, but a device which is commercially viable (i.e. cost and price competitive with currently used non-self retracting devices). Though some devices describe application in the area of blood withdrawal, most contemporary related art is directed toward syringes and like devices. Broadly, related art may be classified into two categories, devices which operate manually and devices which comprise self-contained needle retraction.

Prime examples of prior art needle retraction devices are given as examples in the aforementioned patents. Generally, other than acceptance of the type of operation offered by such devices, commercial viability is dependent upon manufacturing cost. Purchase decisions in the area in which these devices are used are very cost sensitive. If gains in either improvement in safety or in labor savings are not found to make a device sufficiently competitive with contemporary competitive items, those devices are usually not found to be commercially viable. Motivation for providing a cost competitive self-retracting needle apparatus coupled with improved safety of use of the apparatus resulted in conception of the instant inventions disclosed herein.

BRIEF SUMMARY AND OBJECTS OF THE INVENTION

In brief summary, devices based upon novel, inventive elements disclosed herein dramatically diminish known major problems resulting from injury-related needle sticks which occur after needle tips are bared as medical needles are withdrawn from a patient at the end of a needle insertion procedure. In preferred embodiments, operation of each invention involves readying a medical needle apparatus and providing access to a medical needle which is enclosed by a cover prior to use. The act of readying the apparatus involves energizing a force storing memory element used in needle retraction and positioning a needle and associated assembly for use. Generally the needle is made available for a medical procedure by physically separating the needle cover from the rest of the apparatus immediately prior to use. Once the cover is removed, the needle is ready for use in a medical procedure (e.g. for acquiring a blood sample or for inserting a catheter).

In preferred embodiments, when the medical procedure is complete, a simple displacement of a portion of the housing, preferably by squeezing that portion of the housing by the thumb and forefinger of one hand, causes the needle to be safely retracted into the housing. It is important to note that in each embodiment the needle can be removed directly from a patient and safely encased in the housing by a simple action of a single hand of an attending technician, leaving the technician's other hand free for other concurrent medical procedures, such as care of the wound site from which the needle is retracted. After retraction, the needle is fully enclosed and contained, permitting the needle apparatus to be laid aside without fear of an inadvertent needle stick while full attentive care is provided to the patient.

Inventions based upon such acts of readying, using and retracting medical needles are disclosed in the above cited art from which this application continues. As inventions disclosed herein comprise critical parts disclosed in that cited art, those portions of that cited art for which patents have been allowed and which comprise teachings related to the inventions disclosed herein are made part of this specification by reference. Novelty of the instant inventions cited herein includes methods and apparatus for extending medical needles for use, for storing energy used in retraction, for handling, retracting and enclosing double ended medical needles (such as phlebotomy needles) and for triggering needle retraction.

In specific forms disclosed herein, this novel invention is the basis for two self-retracting medical needle embodiments specifically dedicated to medical needle devices having a needle point sharpened on both ends (e.g. a phlebotomy device). Both embodiments are employed in transporting, using and retracting a medical needle and confining the entirety of the medical needle within a safe containment housing after use for safe and easy disposal.

Augmenting one of these embodiments is a second housing (such as a phlebotomy barrel) into which the medical needle and related apparatus are temporarily retracted at the end of a medical procedure, but from which the apparatus may be safely separated for easy and safe disposal, permitting the second housing to be used again. In the phlebotomy application using the second housing, devices based upon the invention comprise a plurality of injection molded parts including a front cover, a back cover, a back hub securely affixed about a medical needle having two ends sharpened, a front hub and a sheath. In addition to the medical needle, the device further comprises a force storing, structural element (which may be an elastic tube with a length limiting cord affixed along the length of the tube) and a separate barrel part which is similar in form and function to barrels used with Vacutainers® blood collection tubes, vacuum based sample (blood) collection tubes from Becton, Dickinson and Company of Franklin Lakes, N.J.

The front hub comprises a small front hole through which a needle freely but snugly passes and from which the needle is fully extended from the device for use. The front hub also comprises an annular connecting ring for attachment to one end of the elastic tube. The elastic tube is disposed about a fore part of the medical needle and attached at the other end to the sheath which is disposed as a variably placed enclosure for the back hub and an aft portion of a needle covering snubber. For transport and prior to being readied for use, the back hub and snubber are at least partially disposed within the sheath and biased by the length of the elastic tube such that the fore part of the medical needle remains threaded through the hole thereby protecting the forwardly disposed needle point from inadvertent damage which would occur if the needle were forced through the hole under field use conditions. The back cover is attached to the front hub to provide a cover for the sheath, back hub, snubber, elastic tube and aft portion of the needle. The front cover is connected to the front hub to complete a protected sterile package enclosing a fore portion of the front hub and otherwise exposed fore portion of the medical needle.

The barrel part comprises an aft barrel section which is similar in shape to a Vacutainers® blood collection tubes type barrel, a fore section in which the sheath, hubs, elastic tube (and a portion of the medical needle during a medical procedure) are disposed and a trigger mechanism by which the apparatus is released to retract the medical needle into safe containment of both ends of the needle. After retraction, the fore part and sharpened point of the medical needle are safely captured within the front hub and medical tube while the aft part and sharpened point of the medical needle are likewise safely trapped within the sheath.

To use the device, the back cover is removed from the protected sterile package, exposing the sheath, elastic tube, back hub and snubber. The snubber and sheath are inserted into the fore section of the barrel part until the trigger mechanism retards further travel into the barrel part. The front hub is then forced into contact with a front portion of the back hub thereby compressing the elastic tube, which provides ultimate retraction force for the needle, and forcing the needle further outward from the front hub. Preferably, the front hub is secured by a releasable connection (e.g. threaded, bayonet or snap-on) to the front section. Next, the front cover is removed and the device is readied for a medical procedure.

When the procedure is finished, the trigger is activated to release the back hub into the aft section of the barrel. Thus released, the compressed tube forces the sheath, snubber, back hub and needle aftward from the front section into the aft barrel portion. As part of this action, the sheath is firmly affixed to the back hub in such a manner that it covers and protects the aft needle point. As the needle is retracted, the front point is brought into containment within bounds of the front hub where it is captured as the needle is canted away from the hole in the front hub. The length limited tube, in conjunction with the needle captured therein, forms a rigid, needle safe throw away package comprising the needle, tube, sheath, snubber and back and front hubs.

A second embodiment comprises a self-contained phlebotomy device having a barrel part which is manufactured and shipped as an integral part of the device with portions of the throw away package previously mentioned. As such, the barrel part takes the place of and eliminates the need for the back cover. Also, in this embodiment, the front hub may be molded as a part of the barrel part, eliminating the need for yet another individual molded part in the second embodiment. Thus, in the second embodiment, two fewer injection molded parts are required, reducing injection molded parts to as few as four in the second embodiment.

In the second embodiment, the greater portion of the needle, the snubber and the sheath are disposed within the barrel part from the point of manufacture, through shipment and just prior to being prepared for use. To prepare the device for use, a front cover is used to draw the needle, sheath, snubber and associated parts forward until a force storing element (such as an elastic tube) is compressed. A latch is set to maintain the needle in the forward position for use in a medical procedure. Upon completion of the procedure, the medical needle latch is released and the needle and associated parts are retracted into the barrel for disposal as an integral unit. In a manner similar to the disposable portion of the first embodiment, the sheath is locked in position to protect against inadvertent injury by the rear needle point. In the case of the second embodiment, the front needle point is captured inside the fore portion or hub portion of the barrel after retraction of the needle.

In another form, this invention is applied to intravenous (IV) catheters whereby an IV catheter and catheter insertion needle are shielded within a housing prior to use, extended from the housing prior to use and the needle is automatically and safely withdrawn from patient and catheter, providing access to the catheter for a medical procedure. Further, the act of extending the needle and catheter stores energy in an energy storing element for later use in retracting the needle into the housing.

This form takes advantage of the use of a vacuum to act as the basis for a force for retracting the catheter needle making possible production of a device which comprises but four injection molded parts. The device comprises an elongated, cylindrical needle containment housing, a simple rear closure for the housing, a catheter insertion needle and needle hub and a cover. Affixed to the hub is a plunger part which, in a manner similar to a syringe, is drawn through the cylindrical housing to create a vacuum within the housing, when the needle is extended from the housing for use in inserting the catheter. The differential force which results from the vacuum/atmospheric interface is used to return the needle to the housing at the end of a medical procedure. Such use of vacuum is disclosed in patent applications and patents from which this application continues, but novelty of this form is found in methods and apparatus used to pull needle and catheter from the housing and in latch and release mechanisms used to trigger needle retraction.

Note that, in a preferred method, each device of the instant invention is triggered by action transverse in direction to the long axis of a needle to cause the needle to be retracted directly from a patient. In a continuing motion, the needle is then safely enclosed in the containment housing.

Accordingly, it is a primary object to provide a novel single use, phlebotomy apparatus comprising an improved safety medical needle retracting device comprising a housing and associated needle cover which, in combination, protect tip integrity and sterility of a medical needle and other internal parts of the device until use and which automatically fully retracts the needle into the housing for safe containment after use.

It is an object of significant importance that the phlebotomy apparatus be approximately the same form and physical volume and be used in substantially the same manner as a standard phlebotomy needle assembly which is in current use in blood acquisition systems which employ vacuum sampling tubes, such as Vacutainers® blood collection tubes available for Becton, Dickinson, and Company Franklin Lakes, N.J.

It is another primary object to provide a needle withdrawal device which protectively covers all sharpened needle points before beginning and after completing a medical procedure.

It is still another primary object to provide a needle withdrawal device which maintains all energy storage and triggerable parts in a relaxed or stress free state until the device is prepared for use immediately prior to a medical procedure.

It is yet another primary object to provide a needle withdrawal device wherein a needle is extended relative to a part which is involved in storing energy, such that the stored energy is later used to retract the needle into a safe housing.

It is an object to provide a powered needle withdrawal device wherein a power providing element of the device is an elastic tube.

It is another object to provide a powered needle withdrawal device wherein a power providing element is a compressible elastic tube.

It is a chief object to provide a needle withdrawal device wherein a needle tip used for percutaneous skin puncture passes but once through an orifice associated with safe needle containment after use, said passage occurring only upon needle retraction.

It is a key object to provide a separate barrel part which is used in combination with a phlebotomy vacuum tube meant for blood acquisition (e.g. in combination with a Vacutainers® blood collection tubes available from Becton, Dickinson and Company Franklin Lakes, N.J.).

It is important that the separable barrel part be made as a single injection molded part.

It is another key object to provide a barrel part which is permanently affixed to and disposable with the blood withdrawal device used in conjunction with a blood acquisition vacuum tube (e.g. a Vacutainers® blood collection made by Becton Dickinson).

It is another object to provide a needle cover for the device which is releasibly affixed to the housing during transport and storage of the device, but which is separable from the housing.

It is an object to provide parts disposed at each end of the device which facilitate manually extending the needle outwardly from the energy storing part to prepare the device for use.

It is another primary object that the device be usable but once and the needle be safely enclosed and all sharpened ends of the needle be protectively covered when retracted.

It is a very important object that the device be made with as few injection molded parts as possible.

It is a major object to provide a quick and easy release apparatus for an IV catheter device.

It is an object to provide a needle withdrawal device for an IV catheter needle wherein power for withdrawing the needle is a vacuum within a housing produced by extending the needle from the housing.

It is an object to provide a trigger release button which is an integrally molded part of the housing.

It is still another object to provide a means for seeing a blood "flashback" within the IV catheter device as influent blood courses into the device from a pierced blood vessel.

These and other objects and features of the present invention will be apparent from the detailed description taken with reference to accompanying drawings.

BRIEF DESCRIPTION OF THE DRAWINGS

FIG. 3 is a perspective of a back cap of the apparatus seen in FIG. 1.

FIG. 4 is a perspective of a front cap of the apparatus seen in FIG. 1.

FIG. 5 is a front perspective of a forward needle hub seen in cross section in FIG. 2.

FIG. 5A is a rear perspective of the forward needle hub seen in FIG. 5.

FIG. 5B is a front elevation of the forward needle hub seen in FIG. 5.

FIG. 5C is a rear elevation of the forward needle hub seen in FIG. 5.

FIG. 23 is a perspective comprising an embodiment of a rear needle hub which includes a locking feature which impedes forward movement of a sheath (not shown).

FIG. 24 is a cross section of the rear needle hub seen in FIG. 23.

FIG. 37 is a cross section of the device of FIG. 35 with medical needle extended and cover removed and ready for use.

FIG. 38 is a section of a rear needle hub of the device seen in FIG. 35.

FIG. 39 is a section of a central portion of the forward hub showing an asymmetric tubing connection embodiment which retards a retracted needle from reentering a needle pathway orifice in the forward hub.

DETAILED DESCRIPTION OF THE ILLUSTRATED EMBODIMENTS

In this description, unless a specific object is referenced, the term proximal is used to indicate the segment of a device normally closest to the patient when it is being used. In like manner, the term distal refers to the other (away from the patient) end. Reference is now made to the embodiments illustrated in FIGS. 1–41 wherein like numerals are used to designate like parts throughout. In some cases, parts having similar form and function to parts earlier cited are enumerated with prime numerals of the earlier cited parts.

Figure 1:
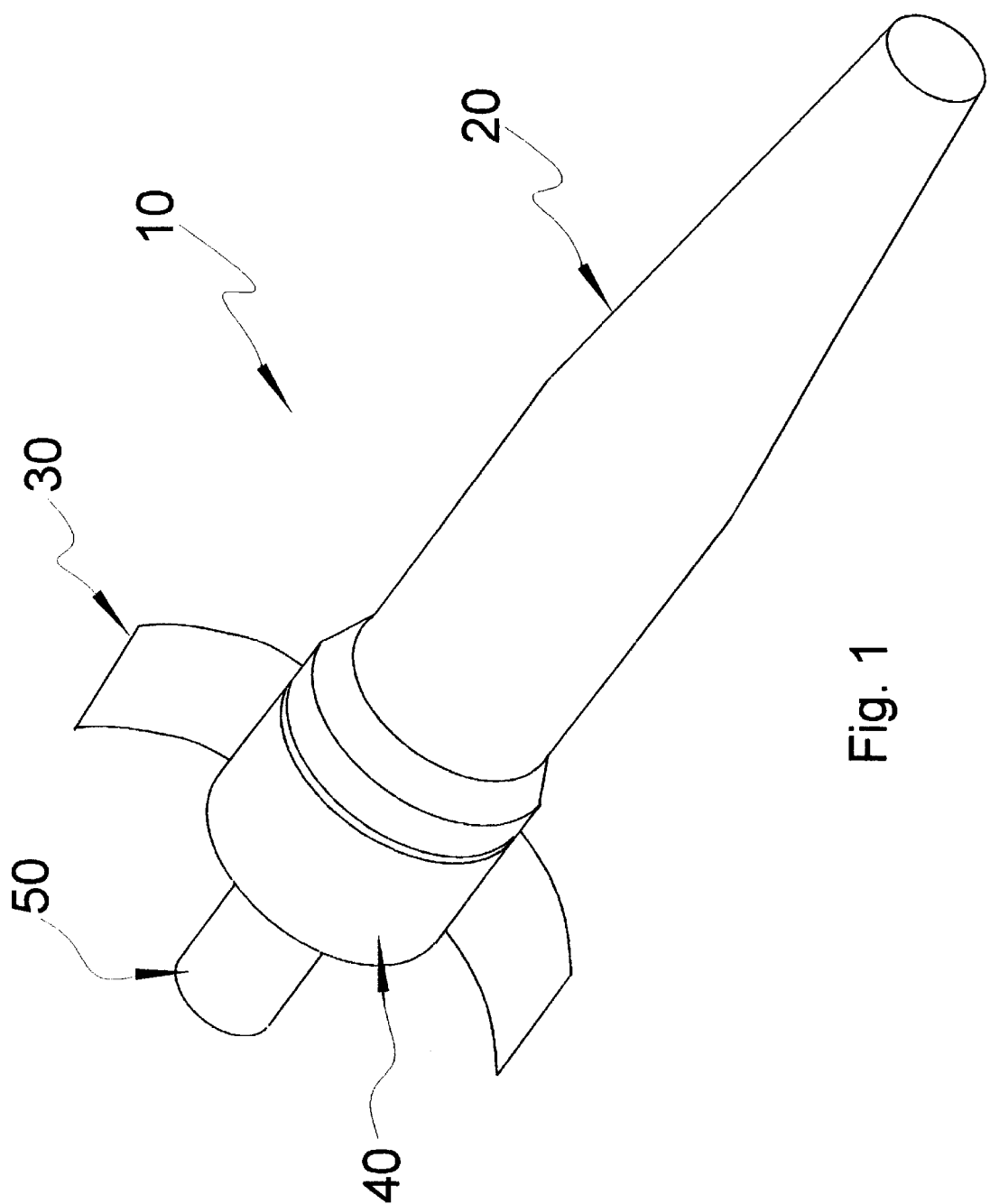
FIG. 1 is a perspective of a safety replacement needle apparatus for a medical phlebotomy procedure.

Reference is now made to FIG. 1 wherein an embodiment of a disposable, self-retracting phlebotomy needle assembly 10 is seen. As manufactured and transported, assembly 10 comprises a back, rearwardly disposed or distal cover 20, a seal 30 (seen broken free for clarity of presentation), a front or forwardly disposed hub 40 and a front, forwardly disposed or proximal cover 50. Other parts, hidden within assembly 10 are seen in cross section in FIG. 2. These internal parts comprise a back or rearwardly disposed hub 60, a phlebotomy needle 70 securely affixed to hub 60, an elastic tube disposed about needle 70 and securely affixed to hubs 40 and 60, a snubber 80 disposed about a distally sharpened end 82 of needle 70 and a sheath 90 which protectively encloses snubber 80 and end 82.

Figure 12:
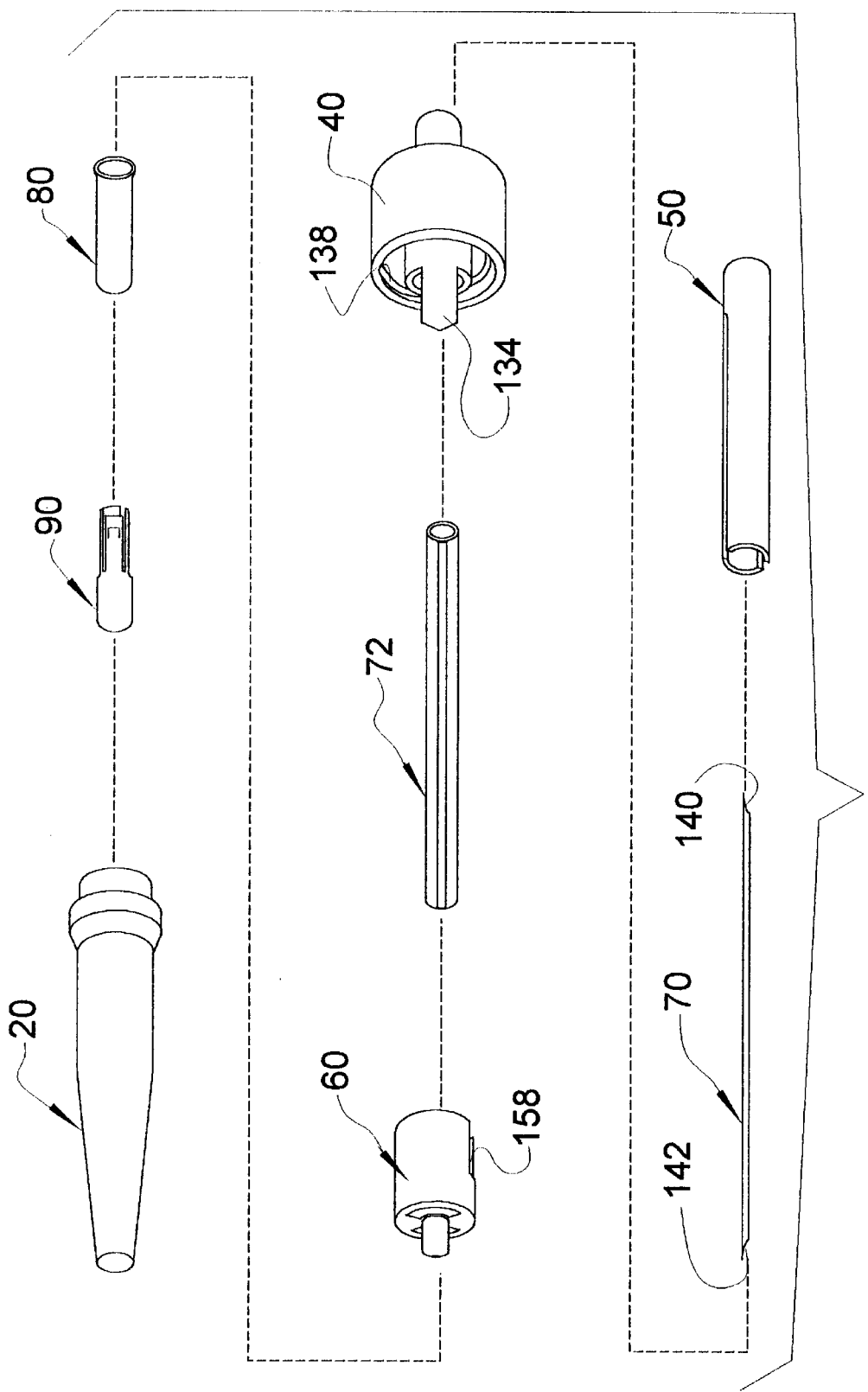
FIG. 12 is an exploded perspective of the phlebotomy needle components seen in FIG. 2.

Each of the above named parts of assembly 10 are seen as individual components in FIGS. 3–11 and an exploded view of all of the parts in an exploded configuration is seen in FIG. 12.

Referring to FIG. 3, back cover 20 is seen to comprise an elongated, cylindrical housing which having a blunt distal end 92 attached to a raised portion 94 by an elongated cylindrical section 96. Cover 20 further comprises a hollow interior surface 98, best seen in FIG. 2. Proximally, cover 20 necks down to a hollow cylindrical section 100 of smaller radius than portion 94. The purpose and function of section 100 is clearly disclosed hereafter. Back cover 20 is preferably made from a resilient, structurally sound synthetic resonant material. For example, medical grade polypropylene may be used, but other plastic materials such as acrylics and polycarbonates can be used when economies of materials cost are compatible with resultant parts cost.

Found in FIG. 4 is a perspective of front cover 50. Cover 50 comprises a closed proximal end 102 which is affixed to a hollow cylindrical section 104. Distal from section 104, cover 50 is split into a pair of elongated legs 106 and 108, each comprising blunt distal ends 110 and 112, respectively. Front cover 50 is also preferably made from polypropylene, however, as in the case of back cover 20, other structurally stable synthetic resinous materials may be used.

One embodiment of front hub 40 is seen in FIGS. 5 and 5A–C. In oblique perspective in FIG. 5, the proximal end of hub 40 is seen to comprise a superior arched slot 114 and an inferior arched slot 116 surrounding a front hub segment 118. Segment 118 joins slots 114 and 116 at a planar front face 120. As best seen in a combination of FIGS. 2, 5, 5B and 5C, front hub segment 188 is a hollow cylinder closed proximally by a slitted end 122. End 122 comprises an "X" cut 124 which provides a closable pathway through which needle 70 is retracted in safe containment. It is important to note that other types of closures or partial closures can be used to block reextension of needle 70 through an end, such as end 122. An example of another type is disclosed in detail hereafter.

Figure 2:
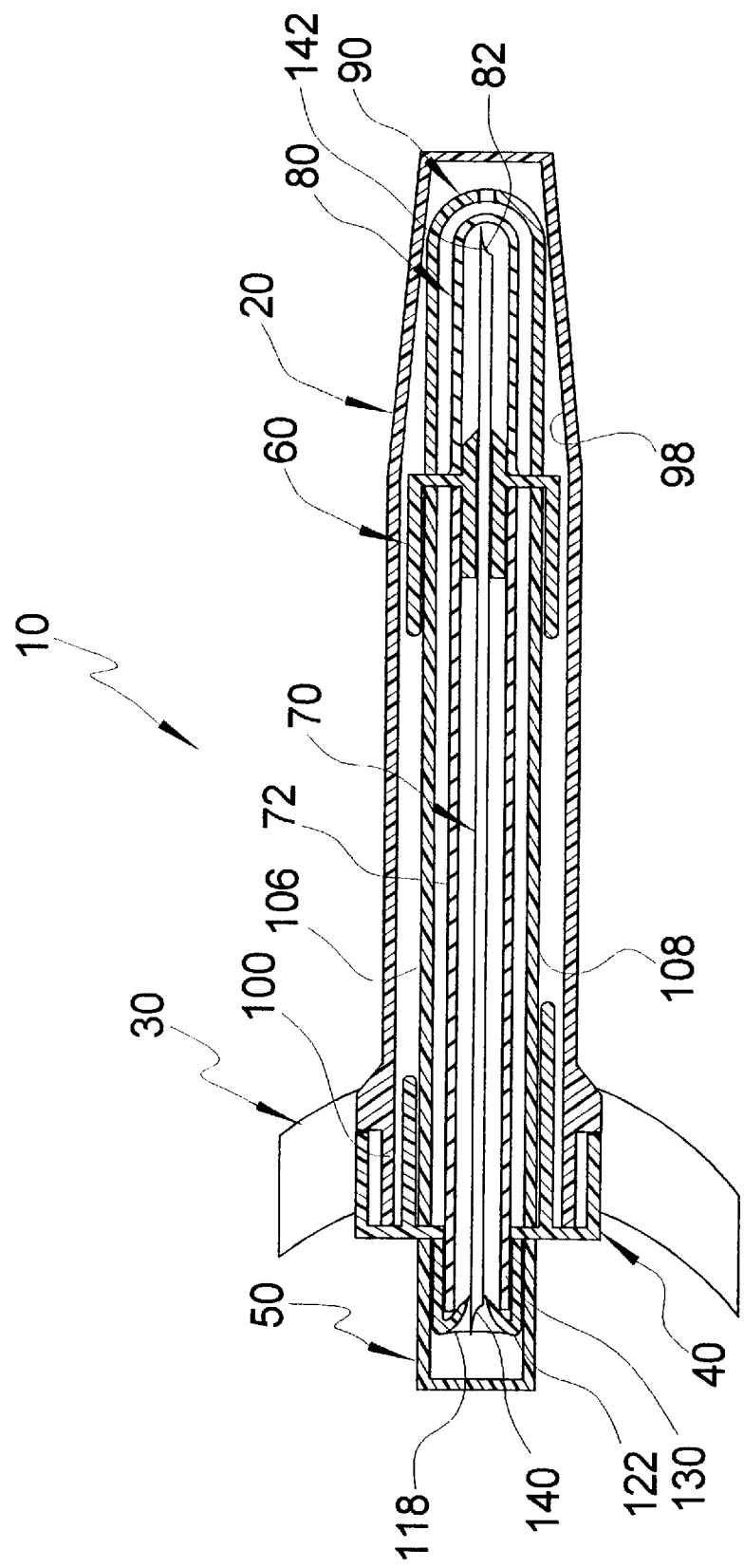
FIG. 2 is a cross section of the apparatus seen in FIG. 1.
Figure 6:
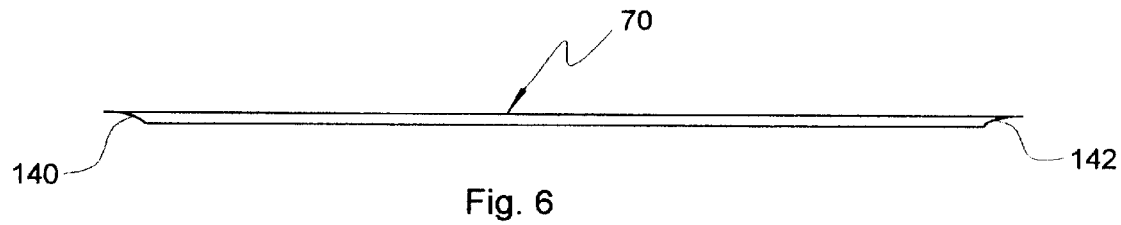
FIG. 6 is a perspective of a double ended needle of the type generally used in medical phlebotomy procedures and seen in FIG. 2.

FIG. 5A shows an oblique perspective of hub 40 rotated approximately 90° from the angle of hub 40 seen in FIG. 5, making the distal or rearwardly disposed surface 126 of hub 40 visible. From the rear, hub 40 is seen to comprise a tube coupler 128 in the form of a hollow raised cylinder for attaching tube 72 to hub 40. Preferably coupler 128 comprises an internally disposed surface 130 which is substantially the same diameter as the external surface of tube 72. Tube 72 residing within surface 130 is seen in FIGS. 2 and 5C. Also, material make-up of hub 40 and tube 72 should be permit ready adhesion of tube 72 to surface 130. Other methods and configurations for connecting tube 72 to hub 40 are within the scope of this instant invention.

Extending distally from a distal end 132 of coupler 128 is a tab 134, best seen in FIG. 5B. The function and purpose of tab 134 is fully disclosed hereafter. Medially and proximally disposed relative to surface 126 is a cylindrical surface 136 which comprises a thread pattern 138 for connecting securely to a barrel. The connecting method is disclosed in detail hereafter. Hub 40 is preferably made from medical grade polypropylene although other materials which are adhesible to tube 72 and which have good structural integrity relative to needle puncture resistance may be used.

Needle 70 is preferably made from a medical grade stainless steel cannula with a percutaneous sharpened tip on a proximal end 140 and a non-coring sharpened tip 142 on distal end 82. Needle 70 should comprise a diameter consistent with contemporary phlebotomy needle diameters and should have sufficient length to provide a desired insertion length (usually one to one and one-half inches (25 to 38 millimeters)) measured as the length extending proximally from a barrel and to provide a desired insertion length (about 0.4 inches (10 millimeters)) within the barrel for introduction into a vacuum sampling tube.

Figure 7:
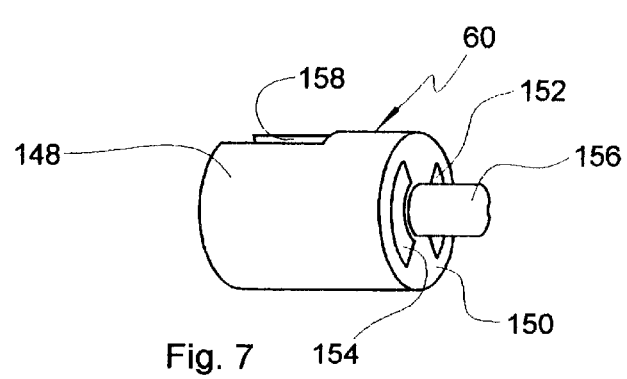
FIG. 7 is a perspective of a rearward needle hub seen in cross section in FIG. 2.

An oblique perspective of rear hub 60 is seen in FIG. 7. As seen in FIG. 7, hub 60 comprises an essentially hollow cylindrical body 148 partially closed on one end by a planar surface 150. Surface 150 comprises a pair of arcuate slots 152 and 154 through which portions of sheath 90 pass to permit compression of snubber 80 and access to end 82 and sharpened tip 142. Distally, hub 60 also comprises a centrally disposed needle hub 156 extended axially outward to support needle 70.

Figure 10:
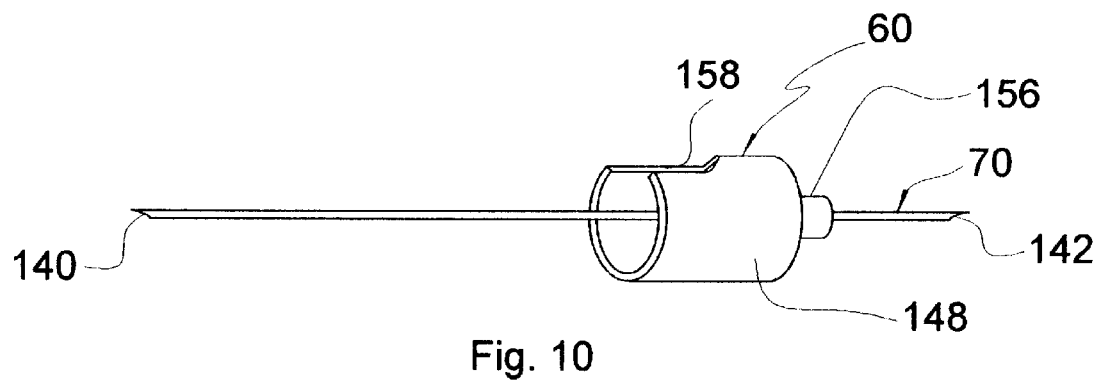
FIG. 10 is a frontal perspective of a combination comprising the medical needle seen in FIG. 6 affixed to the rearward needle hub seen in FIG. 7.
Figure 10A:
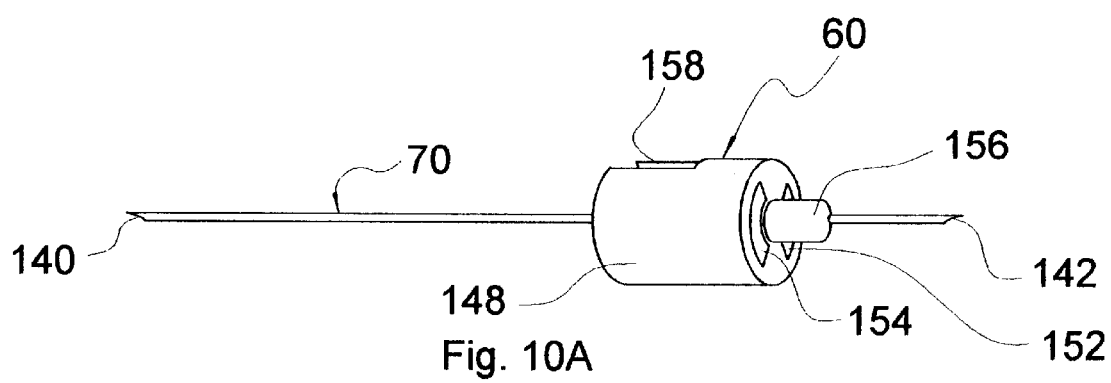
FIG. 10A is a rear perspective of the combination seen in FIG. 10.
Figure 10B:
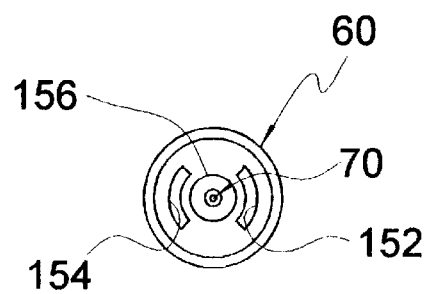
FIG. 10B is a rear elevation of the combination seen in FIG. 10.

A subassembly comprising needle 70 and hub 60 is seen in FIGS. 10 and 10A–C. As seen in FIGS. 10 and 10A, cylindrical body 148 comprises a proximally opening slot 158. Slot 158 is sized and positioned to receive tab 134 when hubs 40 and 60 are aligned and disposed in contact one with the other. It is important to note that when tab 134 is inserted into slot 158, an axial lock is created which causes hubs 40 and 60 to rotate together when either hub is so moved. In an assembled device, needle 70 is securely affixed to hub 60, preferably by an adhesive.

Figure 10C:
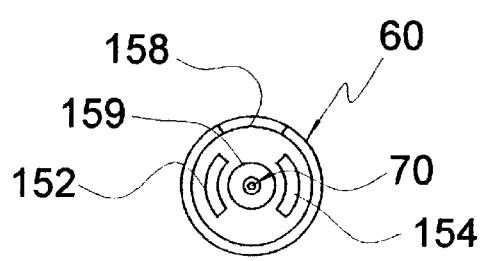
FIG. 10C is a rear elevation of the combination seen in FIG. 10.
Figure 11:
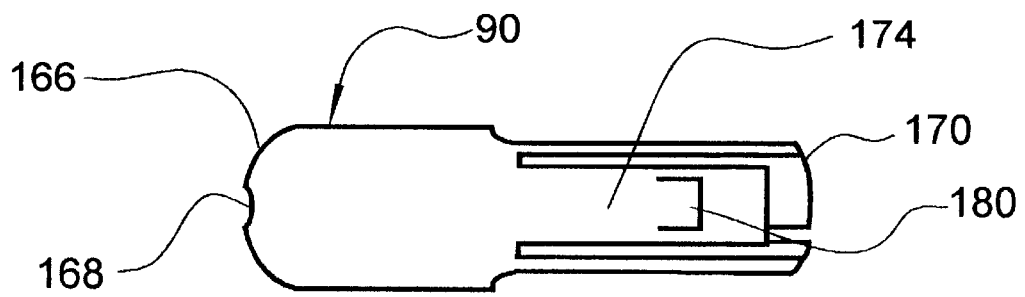
FIG. 11 is a frontal perspective of a shield which protects a rear portion of the medical needle seen in FIG. 6.
Figure 11A:
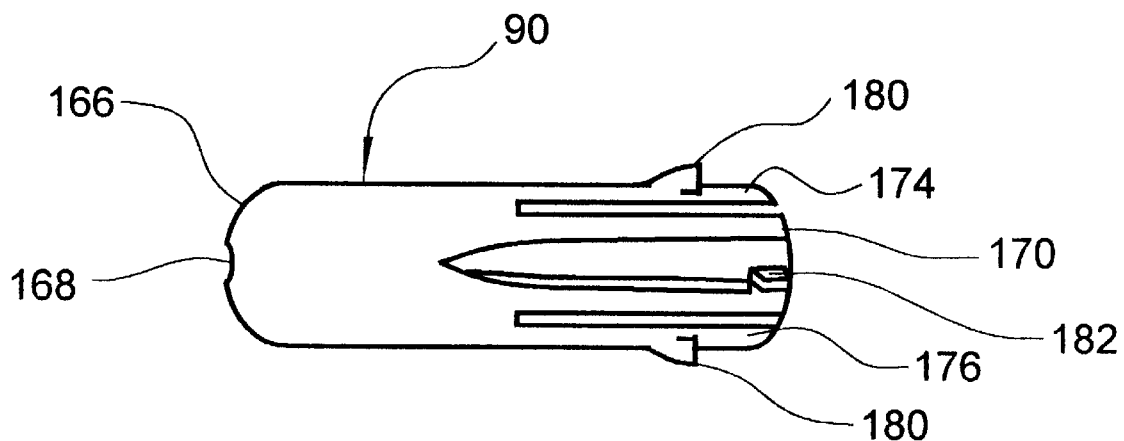
FIG. 11A is a rear perspective of the shield seen in FIG. 11.

As best seen in FIG. 10C, hub 60 comprises a proximally centrally disposed small hub 159 which provides a mount for the distally disposed end of tube 72. Tube 72 is securely affixed at one end to hub 159 and at the other end to coupler 128. Preferably, tube 72 is so affixed by adhesives which are readily commercially available.

Figure 8:
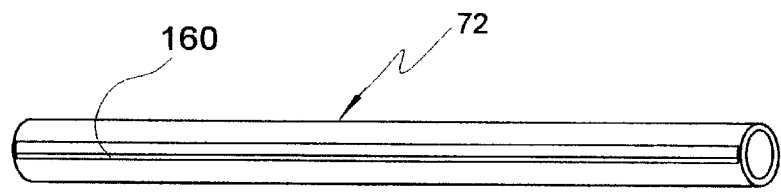
FIG. 8 is a perspective of an elastic tube seen in FIG. 2.

Reference is now made to FIG. 8, wherein tube 72 is seen. Tube 72 is preferably a thin walled, relatively high durometer elastic tube. Though a rather large range of durometers may be used, the preferred range is between 35 and 50 durometer. Though other diameters may be used, the currently preferred diameter is 0.100 inches (2.54 millimeters). The length of tube 72 should be sufficient to completely encase the portion of needle 70 which extends proximally from hub 60. Currently, preferred wall thickness of tube 72 is 0.020 inches (0.51 millimeters). Tube 72 may be made from Kraton, a product of Shell Corporation and available through Shell Chemical Company, 4225 Naperville Road, Suite 375, Lisle Ill. 60532-3660.

As tube 72 is used both as an energy storing medium used in retracting needle 70 and as a length limiting structural member after needle 70 is retracted, a non-elastic member 160 is applied substantially to the entire length or enough of the length of tube 72. Member 160 impedes stretching of tube 72, especially after needle 70 retraction. By this means, when needle point 140 is captured inside hub 40 after retraction, tube 72 cannot be further lengthened to permit access to point 140 which may result in inadvertent injury. Member 160 may be any foldable material which follows changes in tube 72 contour as tube 72 is compressed and which has sufficient tensile strength to retard stretching under manually applied stress. As an example, nylon thread may be used.

Figure 9:
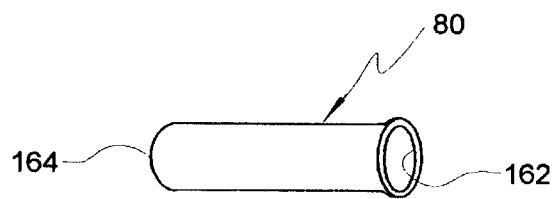
FIG. 9 is a perspective of a snubber of the type generally used in medical phlebotomy needle apparatus and seen in FIG. 2.

An oblique perspective of snubber 80 is seen in FIG. 9. Snubber 80 comprises a proximal open end 162 and a distal end 164. At end 162, snubber 80 is securely affixed to hub 60 about smaller hub 156. End 164 is closed, but is sufficiently thin to permit penetration of tip 142 therethrough. Generally, tip 142 is ground to a non-coring configuration to limit sample contamination which might otherwise result from passage of tip 142 through end 164. Generally, such snubbers are currently available in the art of vacuum based blood draw systems. It is important that snubber 80 be made from an elastic material having a durometer which provides sufficient memory upon deformation to substantially recover its original shape after a blood collection tube is removed after having collapsed snubber 80. As is the case of tube 72, the preferred durometer range for snubber 80 is 35 to 50, although other values of durometer can be used.

Sheath 90 provides an immovable protective cover over snubber 80 before and after drawing a sample. During the process of drawing a sample, sheath 90 must freely move to provide access for an interface between needle 70 and a sample collection tube. Sheath 90 comprises an elongated hollow cylindrical shape closed on a distal end 166 except for an orifice 168 through which tip 142 traverses to interface with the sample collection tube. At a proximal end, sheath 90 comprises a blunt end 170 and a pair of leg parts 174 and 176. Leg parts 174 and 176 each comprise a stop 180. Leg part 176 also comprises a latch 182. The purpose and function of leg parts 174 and 176 and associated stops 180 are fully disclosed hereafter. Catch 182 is designed to be forcibly inserted into a slot, such as slot 152 in hub 60, securely, but slidably, affix sheath 90 to hub 60. Thereafter sheath 90 is prevented from separation from hub 60 without breaking either sheath 90 or hub 60. Such connections of injection molded parts are well known in plastics art. Sheath 90 is preferably made from polypropylene, although other structurally strong, but pliable materials may be used.

Reference is made to FIG. 12 for disclosure of a preferred assembly 10 construction sequence. Though not necessary within the scope of the invention, it is recommended that assembly 10 be put together in the following sequence:

1. Affix tube 72 to hub 40 at coupler 128.
2. Affix tube 72 to hub 60 at hub 159.
3. Insert tip 142 of needle 70 through "X" cut 124 in proximal hub segment 118 of hub 40.
4. Cautiously thread needle 70 through tube 72 and hub 60, taking care to safeguard needle tip 142 from inadvertent contact with portions of either tube 72 or hub 60. Caution: Do not permit tip 140 to pass through "X" cut 124, as such could impair percutaneous performance of needle 70 and would likely result in making assembly 10 useless.
5. Securely affix needle 70 to hub 60 while maintaining position of needle tip 140 proximal to "X" cut 124.
6. Insert leg parts of cover 50 through slots 114 and 116 until disposed relative to hub 60 as seen in FIG. 2. Apparatus and method for interlocking cover 50 with hub 60 to maintain needle point 140 proximal to hub 40 is disclosed hereafter.
7. Affix snubber 80 to hub 60.
8. Affix sheath 90 about snubber 80 to hub 60.
9. Distally dispose back cover 20 over the distally disposed parts of assembly 10 as seen in FIG. 2.
10. Affix a seal 30 (preferably paper) about interfacing parts of hub 40 and cover 20 also as seen in FIG. 2.
11. To preserve intrapackage sterility, it is preferable that a fit between hub segment 118 and the proximal portion of cover 50 be sufficiently tight to provide a sterile barrier and hub segment 118 and cover 50 be heat staked to assure maintenance of sterility prior to use.

Thus assembly 10 is complete and ready for transport to a site of use.

Figure 13:
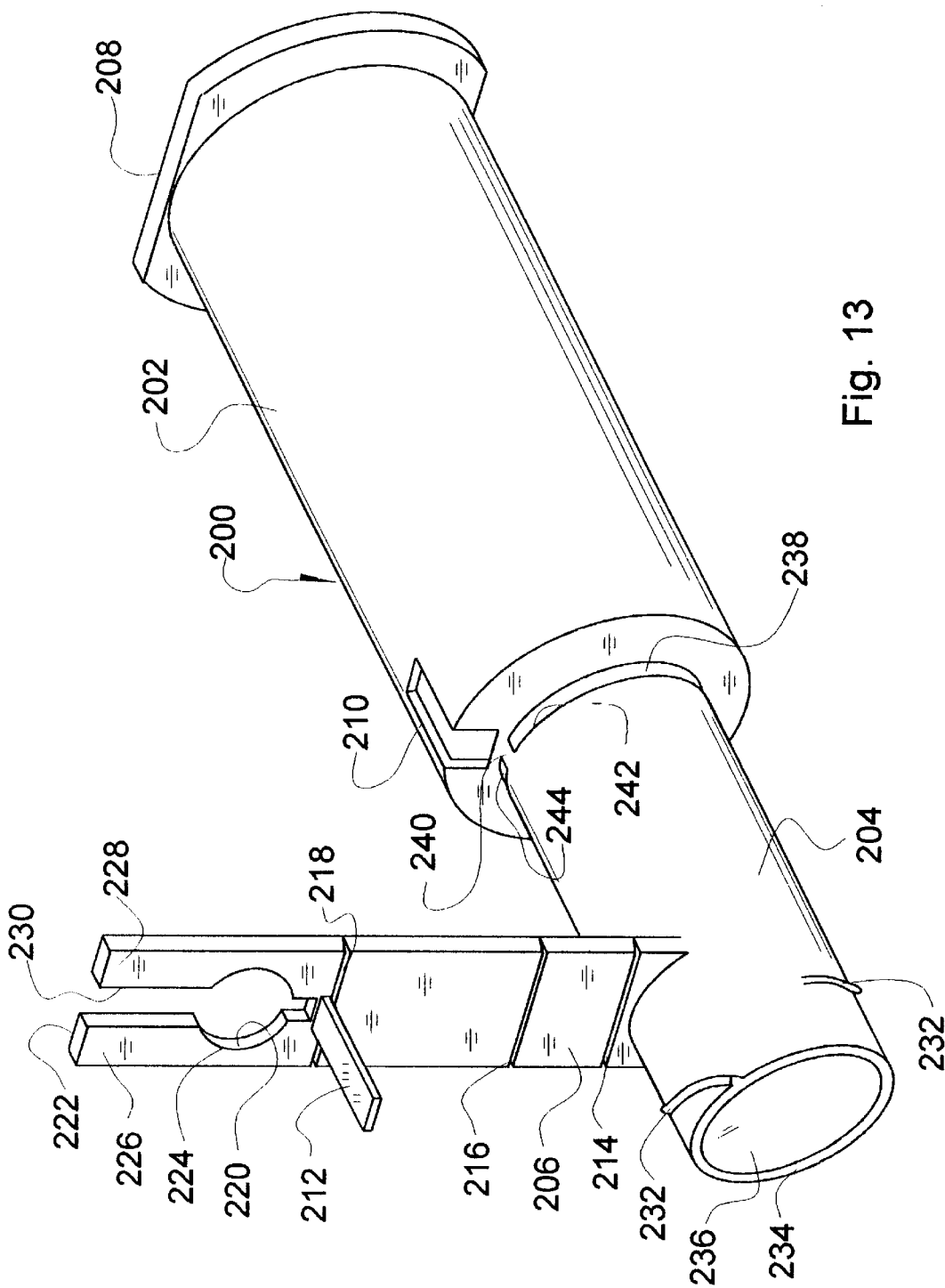
FIG. 13 is an as molded perspective of a phlebotomy barrel used with the medical phlebotomy needle apparatus.
Figure 14:
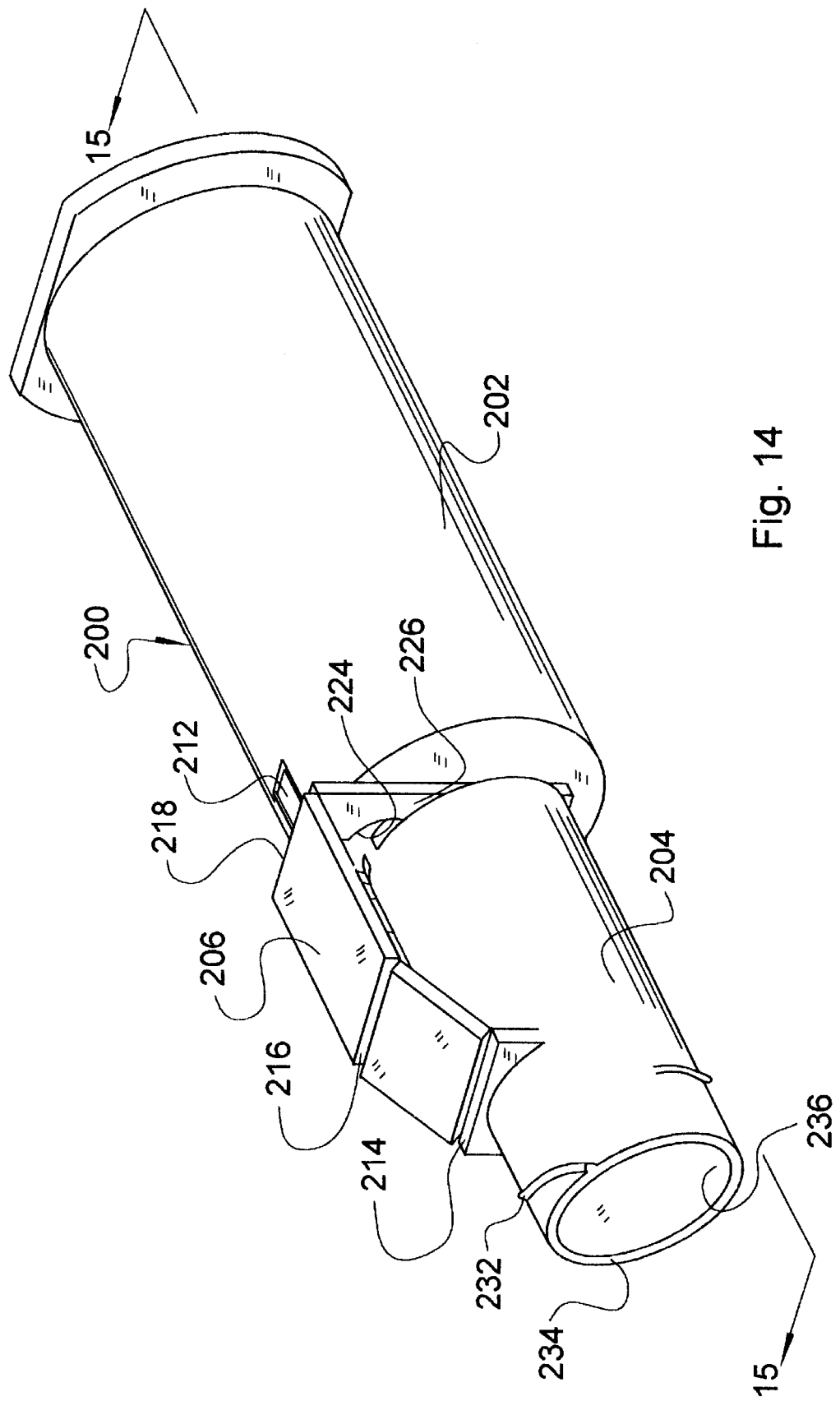
FIG. 14 is a perspective of the phlebotomy barrel seen in FIG. 13 with a portion of the barrel folded into position for use.
Figure 15:
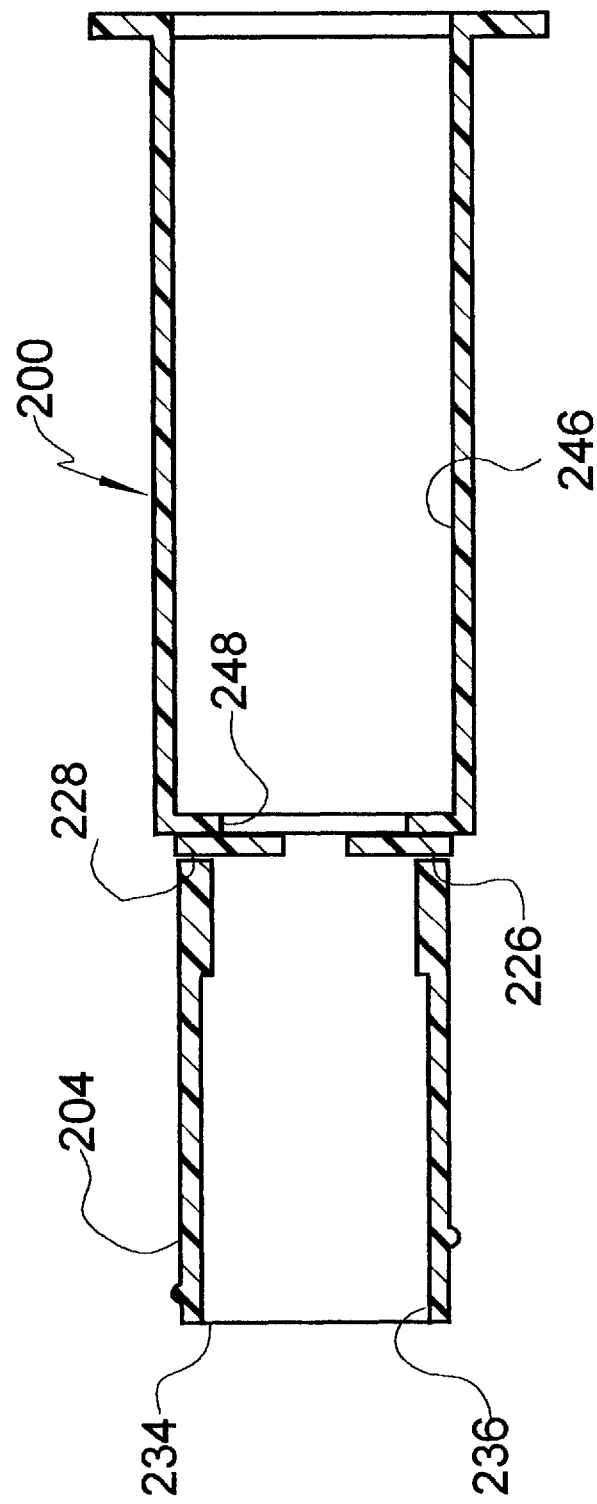
FIG. 15 is a cross section taken along lines 15—15 in FIG. 14.

In blood sampling procedures, assembly 10 is used with a barrel 200, seen in FIGS. 13–15. Barrel 200 is preferably made as a single injection molded part. Barrel 200 may be made from polypropylene.

As seen in FIG. 13, barrel 200 comprises a barrel part 202, an elongated neck segment 204 and an extended latch and trigger strip 206. Barrel 200 is similar in form and function to barrels used with Vacutainers® blood collection tubes (blood sampling tubes from Becton, Dickinson and Company of Franklin Lakes, N.J.). Barrel 200 further comprises a distal sampling tube access end 208, a slot 210 which is used in combination with a tab 212, which is an integral part of strip 206, to detect presence of a sampling tube in part 202 and thereby impede triggering retraction of needle 70 as is more completely disclosed hereafter. It should be noted that slot 210 and tab 212 are optional as such an impedance is not specifically required within the scope of the invention.

Strip 206 may be molded as seen in FIG. 13 or in other modes as determined by molding constraints. Strip 206 may also be molded as a separate part and attached during barrel 200 assembly; however, it is presently preferred to mold barrel 200 in total as a unit. Strip 206 comprises a plurality of living hinges (of which hinges 214, 216 and 218 are examples). Strip 206 also comprises an opening 220 (seen as an upside down keyhole in FIG. 13) inferiorly disposed to a superiorly blunt extremity 222. Opening 220 comprises a substantially circular portion 224 which is of sufficient diameter to pass rear hub 60 and tube 72. Superiorly to opening 220, strip 206 comprises a pair of legs 226 and 228 to define a rectangular opening 230 through which hub 60 cannot pass.

Not also that segment 204 comprises a proximally disposed thread 232 which is used in combination with thread pattern 138 to form a secure, but releasible connection between segment 204 and hub 40. Segment 204 also comprises a proximal orifice 234 which provides access to an elongated cylindrical internal surface 236. Further, segment 204 is integrally connected to barrel part 202 at an interface 238 by a pair of indicated by bridges 240. (A lower bridge 240 is not shown in FIG. 13.) Juxtaposed bridges 240 are a pair of slots 242 and 244, each slot having a width adequate for passage of a portion of strip 206.

As a final step in assembly of barrel 200, hinges 214, 216 and 218 of strip 206 are folded and extremity 222 and legs 226 and 228 are inserted into respective slots 244 and 242. Note, as seen in FIG. 14, as folded and inserted into slots 242 and 244, strip 206 is spring biased such that circular portion 224, which can pass hub 60, is superiorly disposed to a passageway defined by cylindrical surface 236.

Reference is made to FIG. 15 where, in cross section, blocking of the passageway between cylindrical surface 236 and an internal cavity 246 of barrel part 202 by legs 226 and 228. Note that barrel part 202 comprises an access orifice 248 distal to a plane defined by legs 226 and 228.

Figure 16:
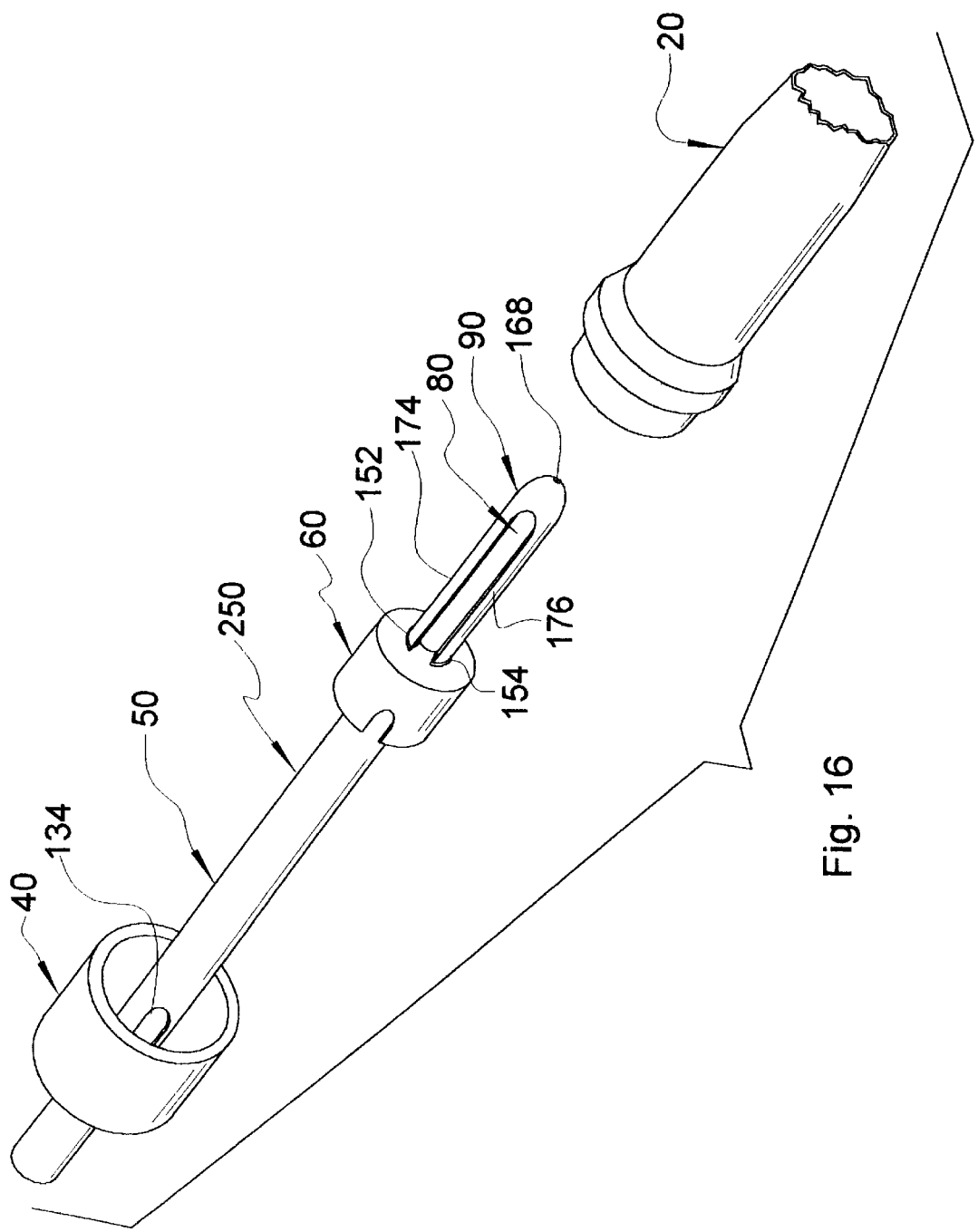
FIG. 16 is a perspective of the apparatus of FIG. 1 with the back cap seen in FIG. 3 removed to ready an insertable portion of the safety needle apparatus for insertion into a barrel for subsequent use.
Figure 17:
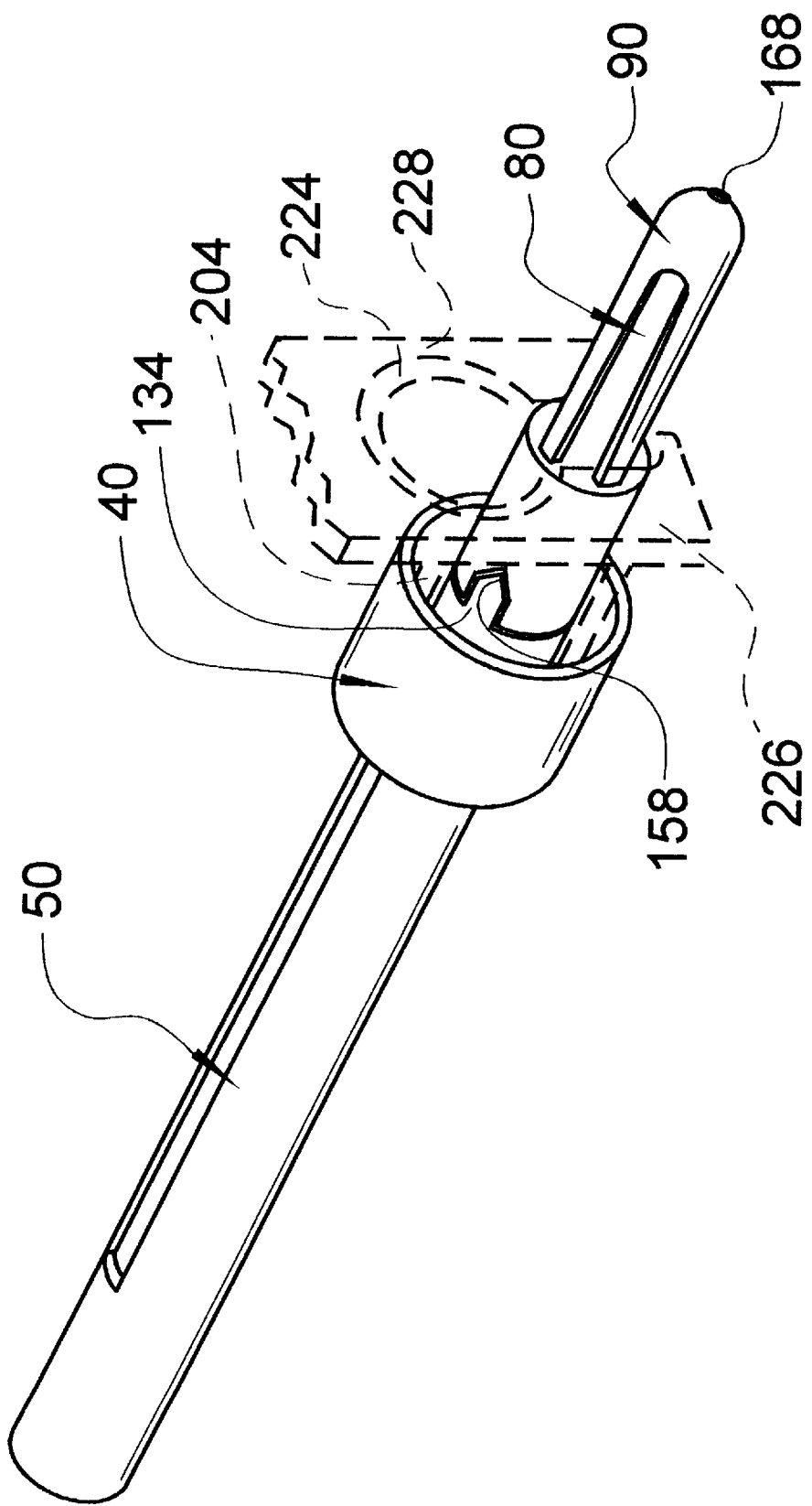
FIG. 17 is a perspective of the insertable portion of the safety needle apparatus in a state after insertion into the barrel.

To prepare assembly 10 for use with barrel 200, rear cover 20 is removed from a remaining portion 250 of assembly 10, as seen in FIG. 16, after breaking seal 30 which is not shown for clarity of presentation. Next, portion 250 is inserted through orifice 234 into barrel segment 204, sheath 90 being inserted first. Note, in FIG. 17, that legs 226 and 228 (shown by dashed lines) block further insertion causing hub 40 to be pushed into contact with hub 60 and tab 134 to be engaged in slot 158. This engagement is important for a number of reasons, but primary among them is to assure that the angular disposition of hub 60 relative to hub 40 is controlled and known. As it is considered to be critical by most medical technicians that needle tip 140 be in a predetermined orientation for use.

Figure 18:
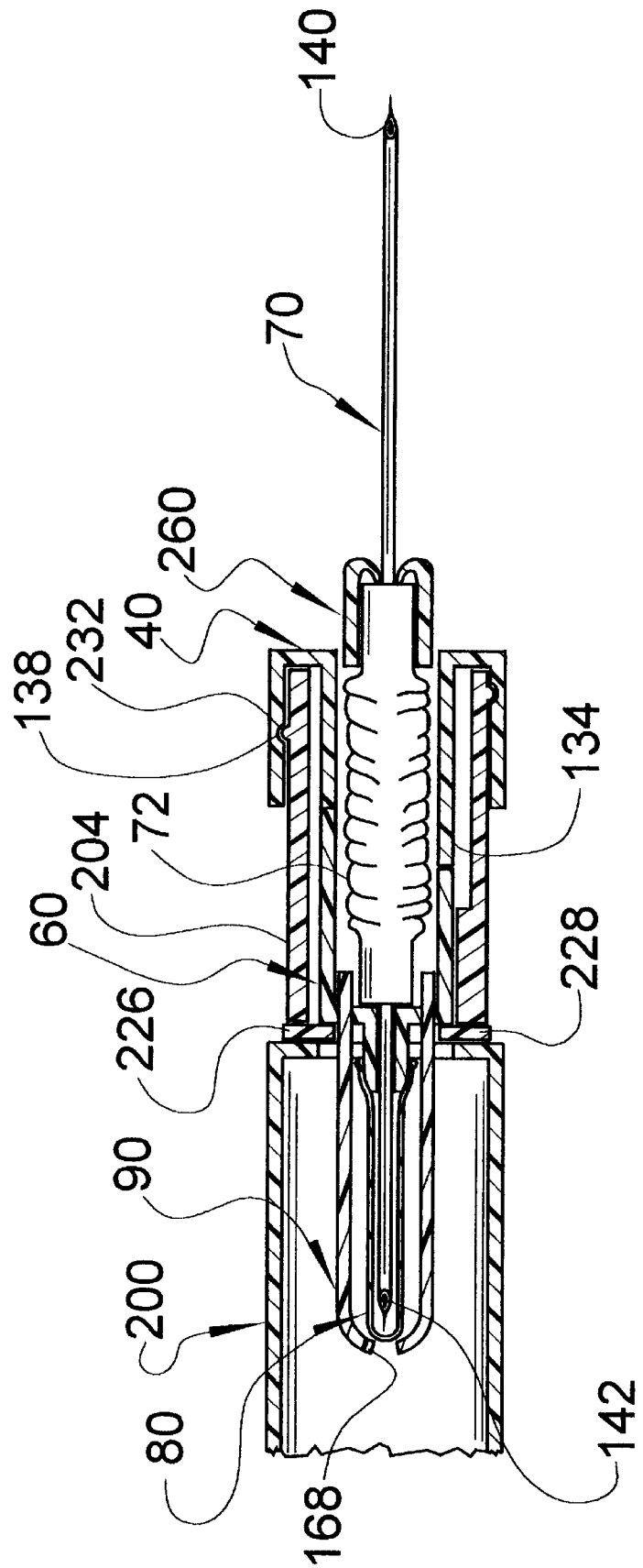
FIG. 18 is cross section of safety needle apparatus disposed in the barrel.

Pushing hub 40 into contact with hub 60 results in compression of tube 72 as is clearly seen in FIG. 18. Hub 40 is securely, but releasibly, affixed to barrel segment 204 by threaded members 138 and 232. As it is important that the axial orientation of needle tip 140 be known and controlled, care must be taken to assure proper orientation of hub 40 relative to barrel 200 when hub 40 is finally affixed to segment 204. For this reason, bayonet or slide-in catching joints may be preferred to connect hub 40 to segment 204.

When hub 60 is pressed hard against legs 226 and 228, stops 180 are depressed inward by legs 226 and 228 permitting leg parts 174 and 176 of sheath 90 to slide freely through slots 152 and 154, respectively, of hub 60. In this manner, sheath 90 is freely displaced by a sample collection tube and needle tip 142 finds passage through orifice 168 while sheath 90 is engaged between legs 226 and 228, but sheath 90 is locked in place providing safe protection for needle tip 142 when sheath is not so engaged.

Figure 19:
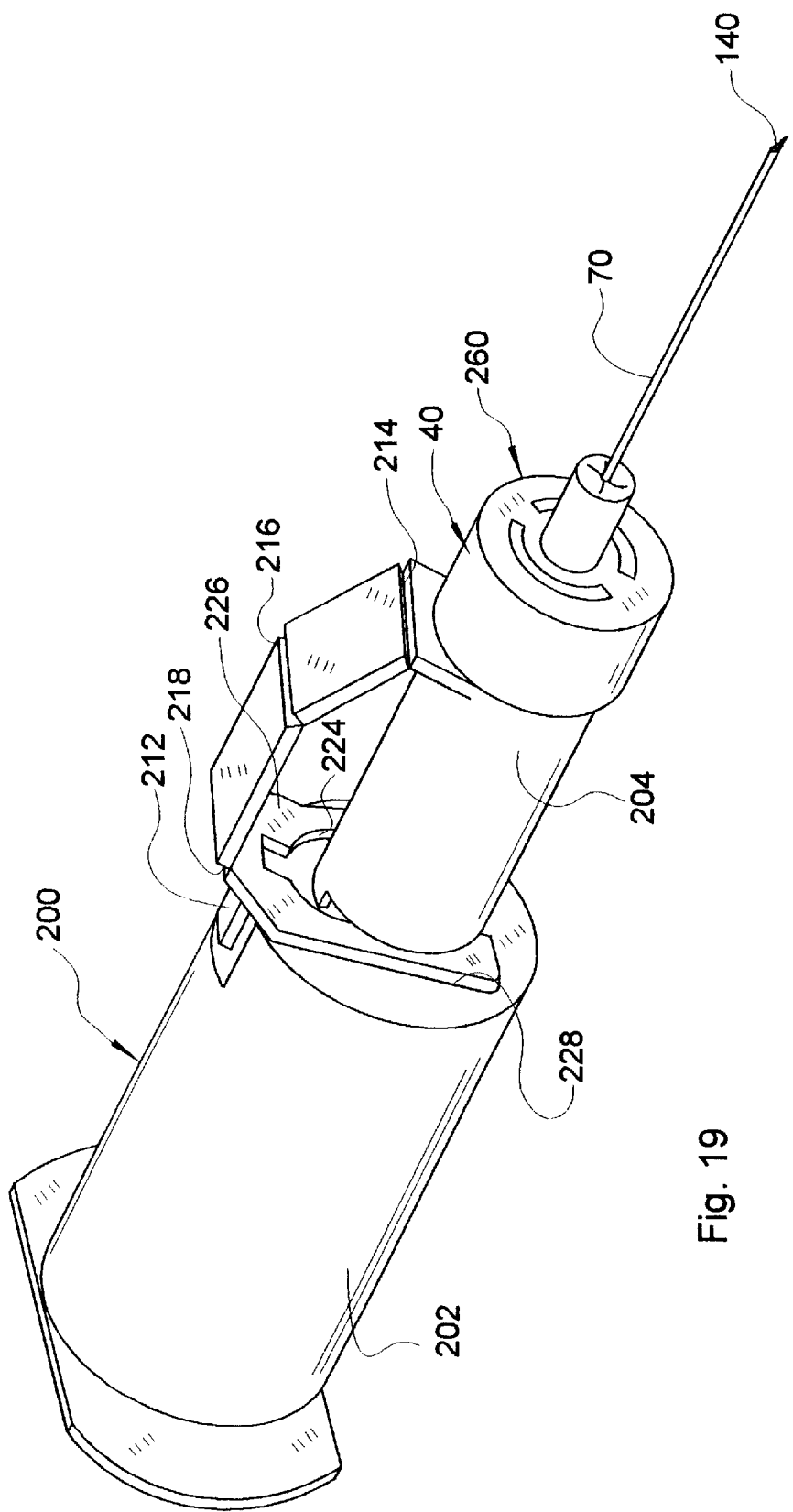
FIG. 19 is a perspective of safety needle apparatus disposed in the barrel with the phlebotomy needle bared and ready for use.

After connecting hub 40 to segment 204, cover 50 is removed to bare needle tip 140 as seen in FIG. 18. With cover 50 removed from portion 250, a residual disposable 260 is mounted securely, but releasibly affixed to barrel 200. A perspective of a barrel 200 with disposable 260 affixed with needle tip 140 bared is seen in FIG. 19.

Figure 20:
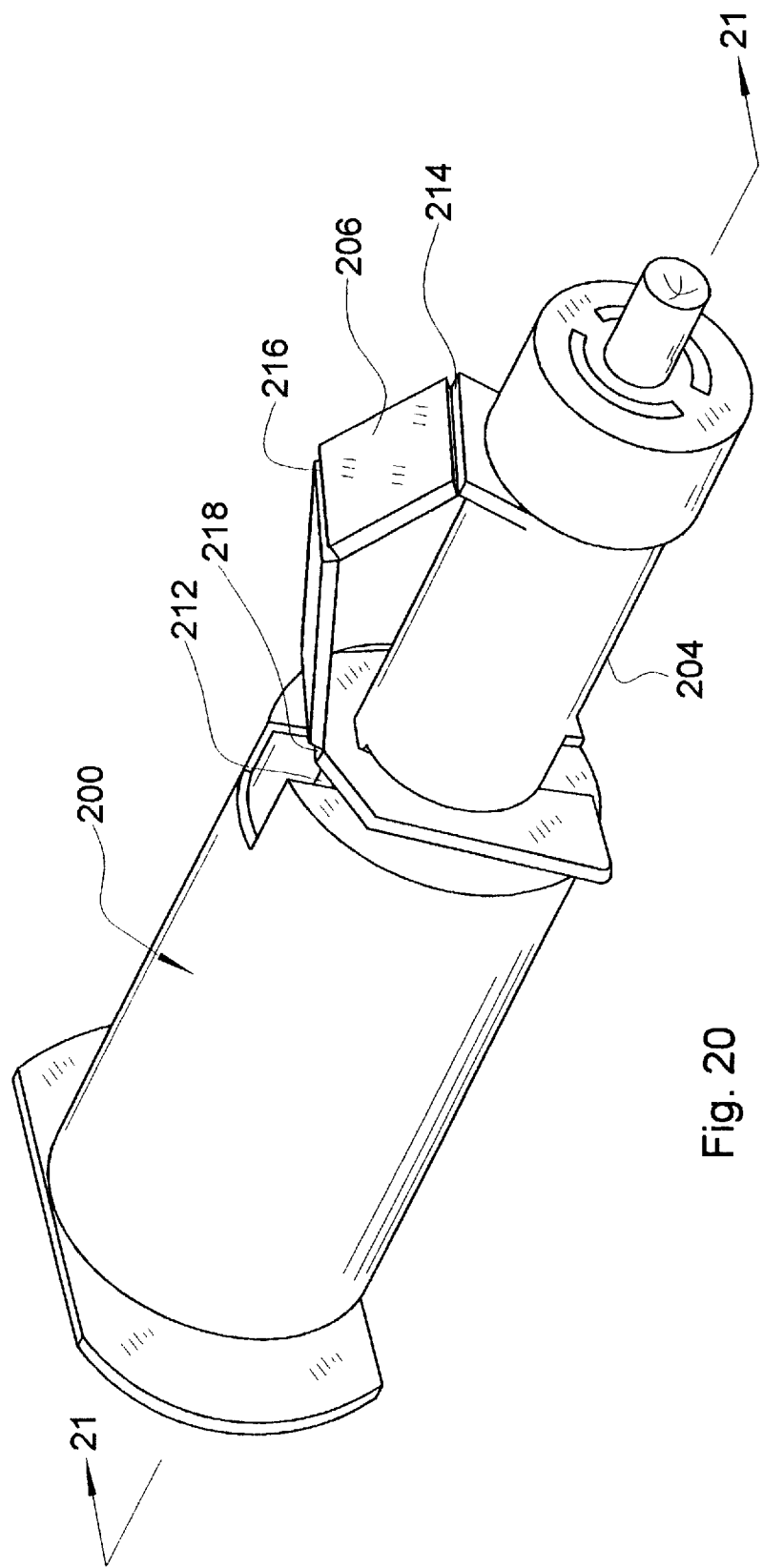
FIG. 20 is a perspective of the barrel and safety needle apparatus after the needle has been retracted into safe containment within the barrel.
Figure 21:
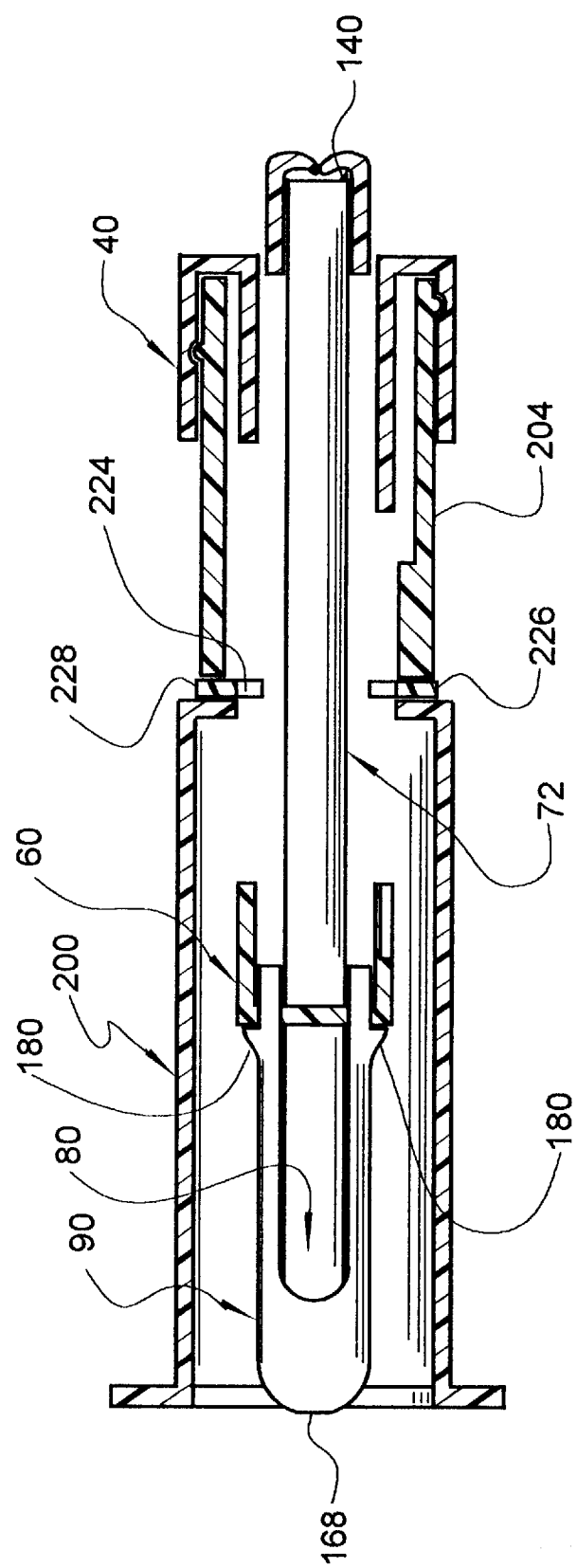
FIG. 21 is a cross section taken along lines 21—21 of FIG. 20.

At the end of a medical procedure, a portion of strip 206 is depressed to align circular portion 224 with hub 60, thereby releasing hub 60 from containment by legs 226 and 228. Resultingly, energy stored in compressed tube 72 causes hub 60 and associated parts of disposable 260 to be displaced distally into barrel 200. When hub 60 is so displaced, needle tip 140 is retracted into safe containment within the confines of hub 40. This state of disposable 260 is best seen in FIGS. 20 and 21. Note that stops 180 are engaged against hub 60 to prevent proximal travel of sheath 90 and thereby protecting needle tip 142 from exposure through orifice 168. Tube 72 acts to fully cover and enclose a proximal portion of needle 70 and needle tip 142. Needle tip 142 also is captured within hub 40. Note also that disposable 260 is converted to a relatively rigid structure by engagement of stops 180 and needle 70 being trapped inside hub 40. Note, as well, that integrity of disposable 260 is further enhanced by non-elasticity of member 160 which restricts further lengthening of tube 72.

Figure 22:
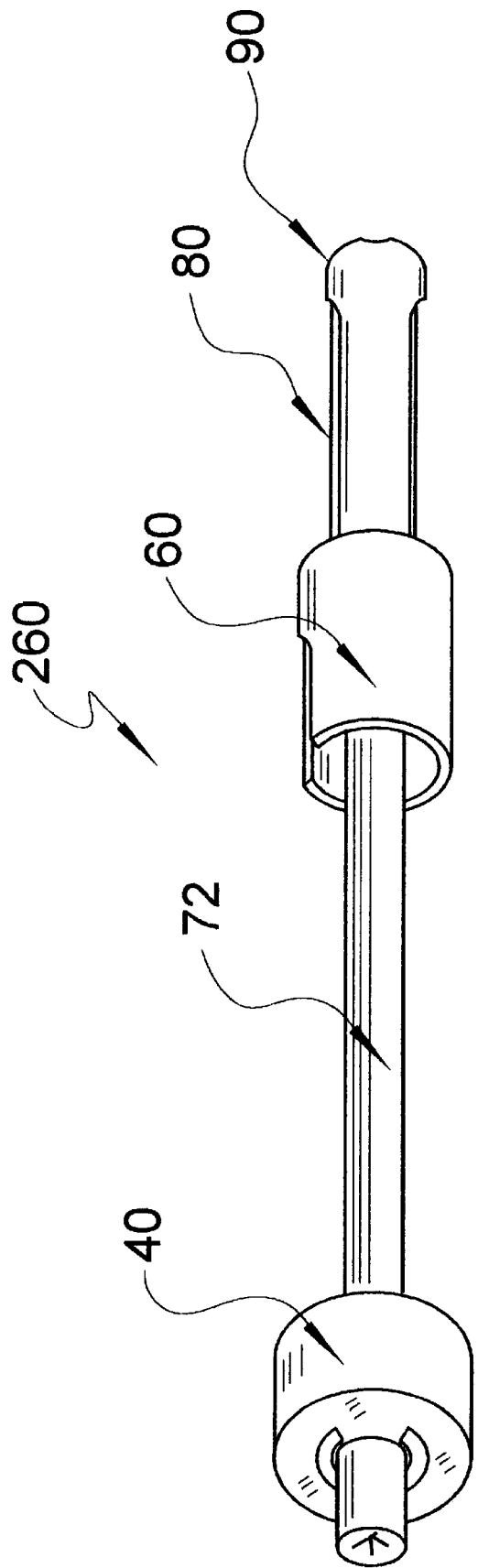
FIG. 22 is a perspective of the safety needle apparatus with both ends of the needle contained and protected for safe disposal.

As hinges 214, 216 and 218 may spring load strip 206 to return to a pre-trigger state after retraction of needle 70, it is necessary to depress strip 206 one more time to remove disposable 260 from barrel 200. Disposable 260 is removed from barrel 200 by unscrewing hub 40 (when a screw attachment is used) from segment 204, depressing strip 206, if necessary, and pulling disposable 260 proximally through orifice 234. The form of disposable 260, removed from barrel 200, is seen in FIG. 22. Note that both needle points are protectively and securely covered for safe disposal.

An example of an alternate embodiment of a back hub 60' comprising another method of impeding free movement of sheath 90 when tube 72 is not compressed (and needle 70 is not disposed for use in a medical procedure) is seen in FIGS. 23 and 24. Hub 60 and 60' are substantially the same in form and function with the exception that hub 60' comprises an inwardly displaced tab 270 which is hingeably connected to a distal portion 272 of hub 60'. A proximal end 274 of tab 270 is biased to be medially disposed against tube 72 when tube 72 is not compressed such that, when tube 72 is compressed, as disclosed above, proximal end 274 is displaced outwardly, away from needle 70. While so displaced, proximal end 274 is engaged against hub 40 and captured thereat.

It should be noted that, tab 270 comprises an interior side 276 and a catch 278 disposed thereon. This catch is disposed to act against proximal end edge 170 and to stop sheath 90 from traveling proximally. Only when tube 72 is compressed and end 274 is engaged against hub 40 is sheath 90 free to travel proximally. Of course, this is the condition when medical needle 70 is disposed for use and when a sampling tube is disposed for use in barrel 200.

Figure 25:
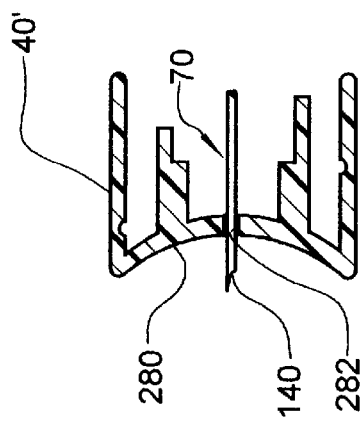
FIG. 25 is a cross section of an oil canning embodiment of a forward hub with oil canning disposed such that a portion of the needle extends forward from the hub.
Figure 26:
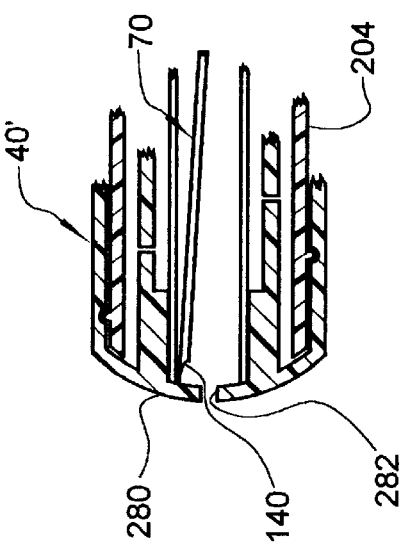
FIG. 26 is a cross section of the forward hub embodiment of FIG. 25 but with oil canning disposed in a convex mode such that the needle is disposed rearward of the hub.

Reference is now made to FIGS. 25 and 26 where an alternate hub form 40' of hub 40 is seen. Hub form 40' is similar in form and function to hub 40, except that, when using hub 40, needle tip 140 is needfully constrained from distally passing through any front barrier of hub 40 by a connection between cover 50 and hub 60 and another connection between cover 50 and hub 40. These two constraints permit tube 72 to be compressed slightly until both connections are broken as a result of inserting assembly 10 portion 250 into barrel 200, thereby biasing needle tip 140 proximally and keeping tip 140 from retracting into hub 40. To eliminate the need for so slightly compressing tube 72, hub 401 comprises a proximal face 280 which has two stable positions. A first position comprising a proximally concave state of face 280 as seen in FIG. 25. A second position comprising a proximally convex state of face 280 as seen in FIG. 26. When not attached to barrel 200, convex face 280 is distally depressed toward hub 60 thereby shortening the effective distance between face 280 and hub 60 and thereby causing needle tip 140 to be proximally disposed relative to face 280.

When hub 401 is connected to segment 204 as earlier disclosed for connecting hub 40 to segment 204, face 280 is forced into the convex state. Note that the change of state does not occur until hub 401 is moved into contact with segment 204, and, therefore needle tip 140 is already extended proximally well beyond face 280. However, when needle 70 is retracted into barrel 200, such as through orifice 282, needle tip is captured within hub 40' as seen in FIG. 26. Use of hub 40' eliminates any need for even slightly compressing tube 72 prior to insertion of portion 250 into barrel 200.

Figure 27:
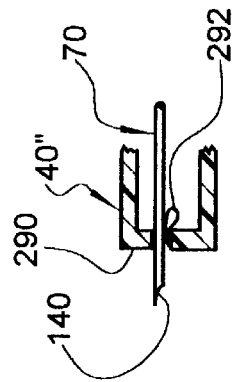
FIG. 27 is a cross section of a segment of front hub comprising an orifice filling plug for impeding forwardly directed needle travel after needle retraction.
Figure 28:
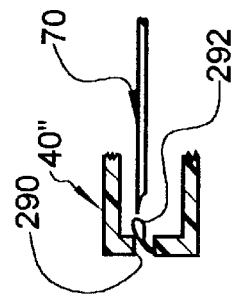
FIG. 28 is a cross section of the segment of FIG. 27 after needle retraction.

Entrapment of needle tip 140 may be accomplished by many different ways within the scope of the invention. As examples, by retracting needle tip 140 through a self closing element (such as previously disclosed "X" cut 124) or by creating a curved resting tube 72 through a shortening bias by non-elastic member 160 or by an internal component housed within segment 204 which biases needle 70 and therefore needle tip 140 toward an inside wall of hub 40. One mechanism for positively impeding escape of needle tip 140 from a front hub (such as hub 40), after needle 70 retraction, is by interposing a part between needle tip 140 and an exit orifice 290 as seen in FIG. 28. Note a front hub 40", which is similar in form and function to hub 40, except for replacing "X" cut 124 with a selectively plugging element, such as element 292, seen in FIGS. 27 and 28. In this case, element 292 is formed by franging most of an initial portion of a plug molded into hub 40" covering a hole space which is to be opened to provide the needle 70 access of orifice 290. As best seen in FIG. 27, sufficient material is left after the frange to permit element 292 to remain hingeably affixed to hub 40" at orifice 290 and to remain biased against needle 70 as long as a portion of needle 70 is disposed proximal to orifice 290. However, after needle 70 retraction, element 292 responds to inherent prefrange memory to hingeable displacement to at least partially plug orifice 290 and impede further proximal travel of needle 70 such that needle tip 140 is safely retained distal to orifice 290.

Attention is now directed to FIGS. 29–34 wherein an embodiment of an extendable and retractable IV catheter device is seen. The IV catheter device derives energy for retraction by a vacuum pulled as a catheter needle is extended for use. Another such vacuum based extendable and retractable catheter is disclosed in patents from which this patent continues. Novelty which is disclosed and claimed herein is specifically limited to apparatus and method for a quick release cover which is used to extend the needle and for a cantilevered trigger release button which is activated to retract the catheter needle.

Figure 29:
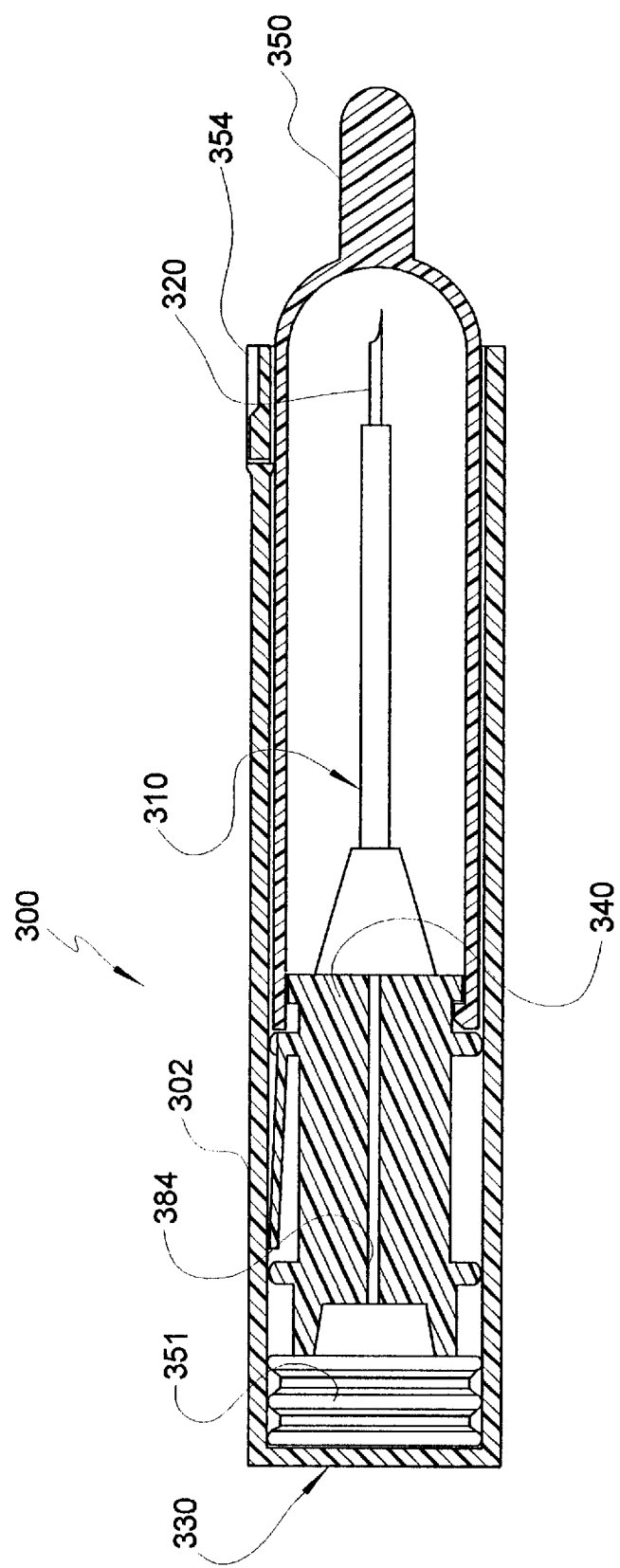
FIG. 29 is a cross section of an extendable medical catheter apparatus.

As seen in FIG. 29 a catheter device 300 requires but four injection molded parts. The parts comprise an elongated barrel 302 from which a catheter 310 and catheter needle 320 are extended for us and into which the catheter needle 320 is retracted for safe disposal, a back disk 330 which closes a rear portion of barrel 302 such that a vacuum can be created therein when a plunger traverses barrel 302, a releasible latch and needle hub 340 and a cover 350 which is used to extend catheter 310 and needle 320 from barrel 302 preparatory to using catheter device 300. Device 300 also comprises a plunger 351 which is similar to a plunger for a disposable syringe and which is securely affixed to needle hub 340.

Figure 30:
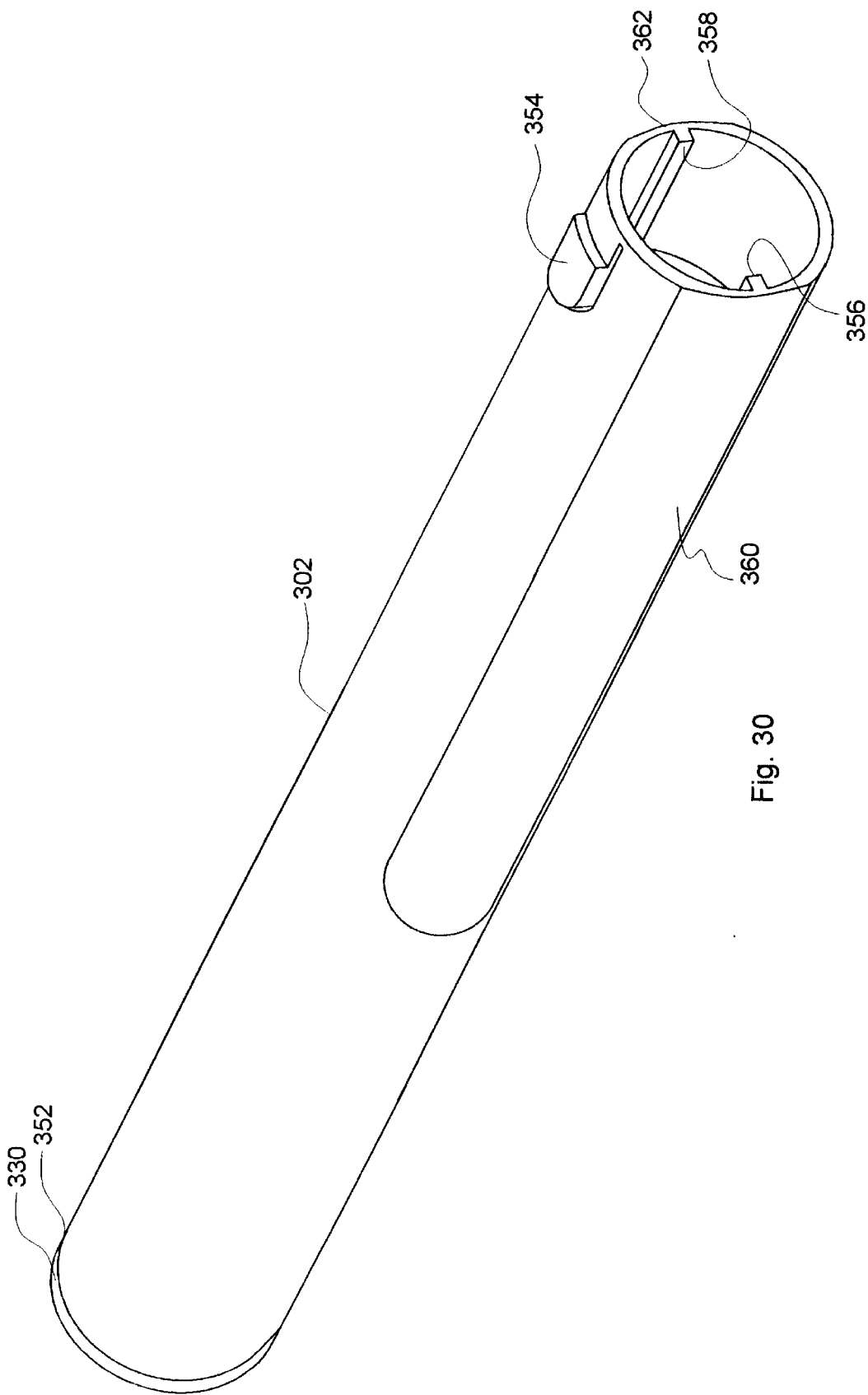
FIG. 30 is a perspective of an elongated cylinder which forms a rearward portion of the catheter apparatus of FIG. 29.

Barrel 302, closed at a distal end 352 by disk 330, is seen in FIG. 30. Both Barrel 302 and disk 330 may be made from polycarbonate, although other materials, which have sufficient structural integrity to combine with plunger 351 to produce a vacuum within barrel 302 as the plunger is pulled within the barrel 302 and to withstand ambient forces associated with the vacuum may also be used. Disk 330 is preferably adhesively affixed to barrel 302. Adhesives for such purposes are well known in the art. Also, as seen in FIG. 30, barrel 302 comprises a cantilevered trigger release button 354, the purpose and function of which is disclosed hereafter. Button 354 is molded as an integral part of barrel 302. Barrel 302 also comprises various rails 356 and 358 and side indentations 360 and 362 which support reliable operation of device 300.

Figure 31:
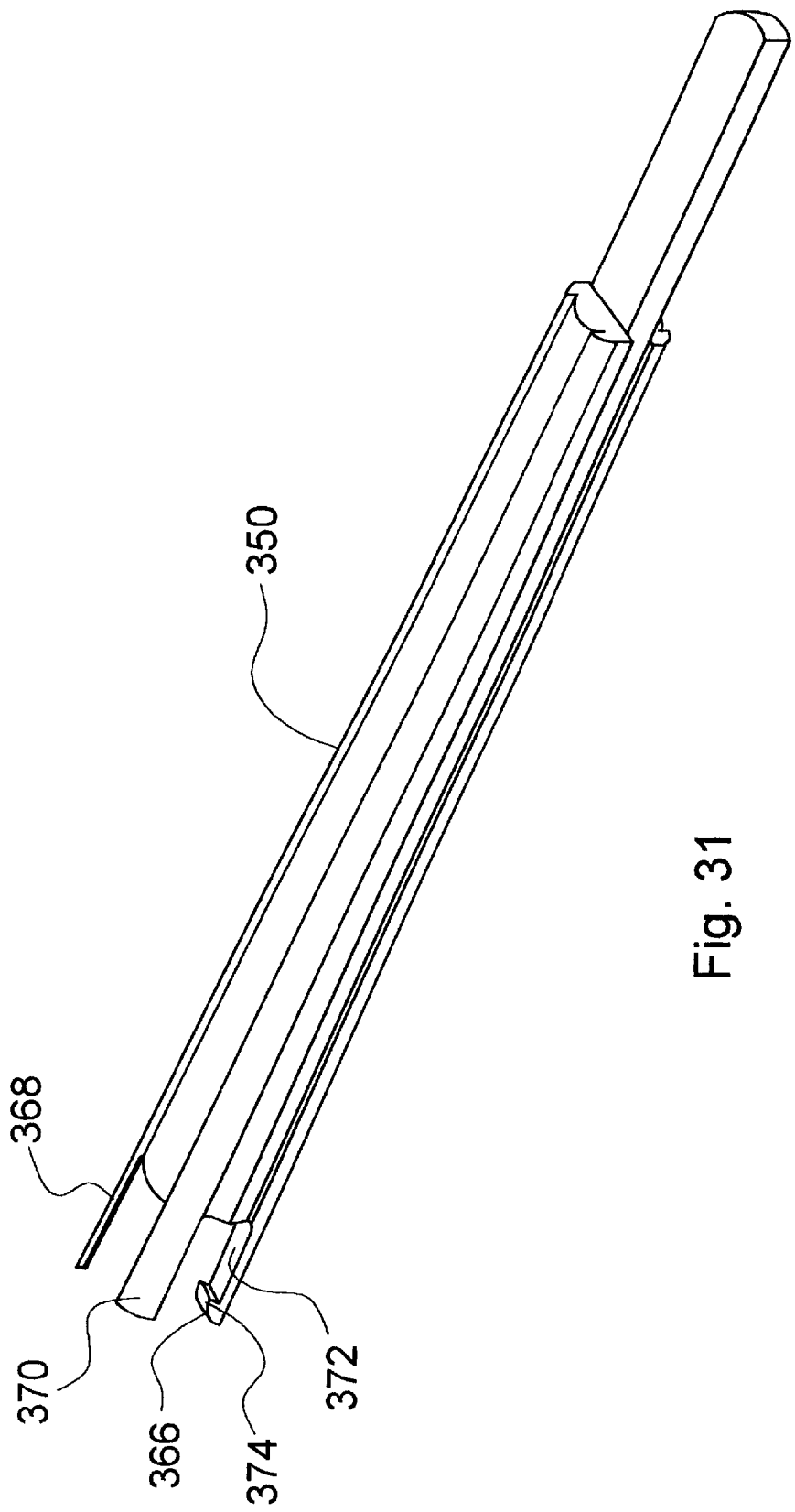
FIG. 31 is a perspective of a forwardly disposed needle cover of the extendable medical catheter apparatus of FIG. 29.

A perspective of cover 350 is seen in FIG. 31. Cover 350 comprises an elongated hollow cylinder 364 which covers and protects prior to and during elongation of device 300 preparatory for use. At a distal end 366, cover 350 comprises three legs, denoted as 368, 370 and 372. Legs 368 and 370 are simple extensions which provide axial support until cover 350 is removed after extension of device 300. However, leg 373 comprises a raised latch element 374, the purpose and function of which is disclosed hereafter. Cover 350 may be made from polypropylene.

Figure 32:
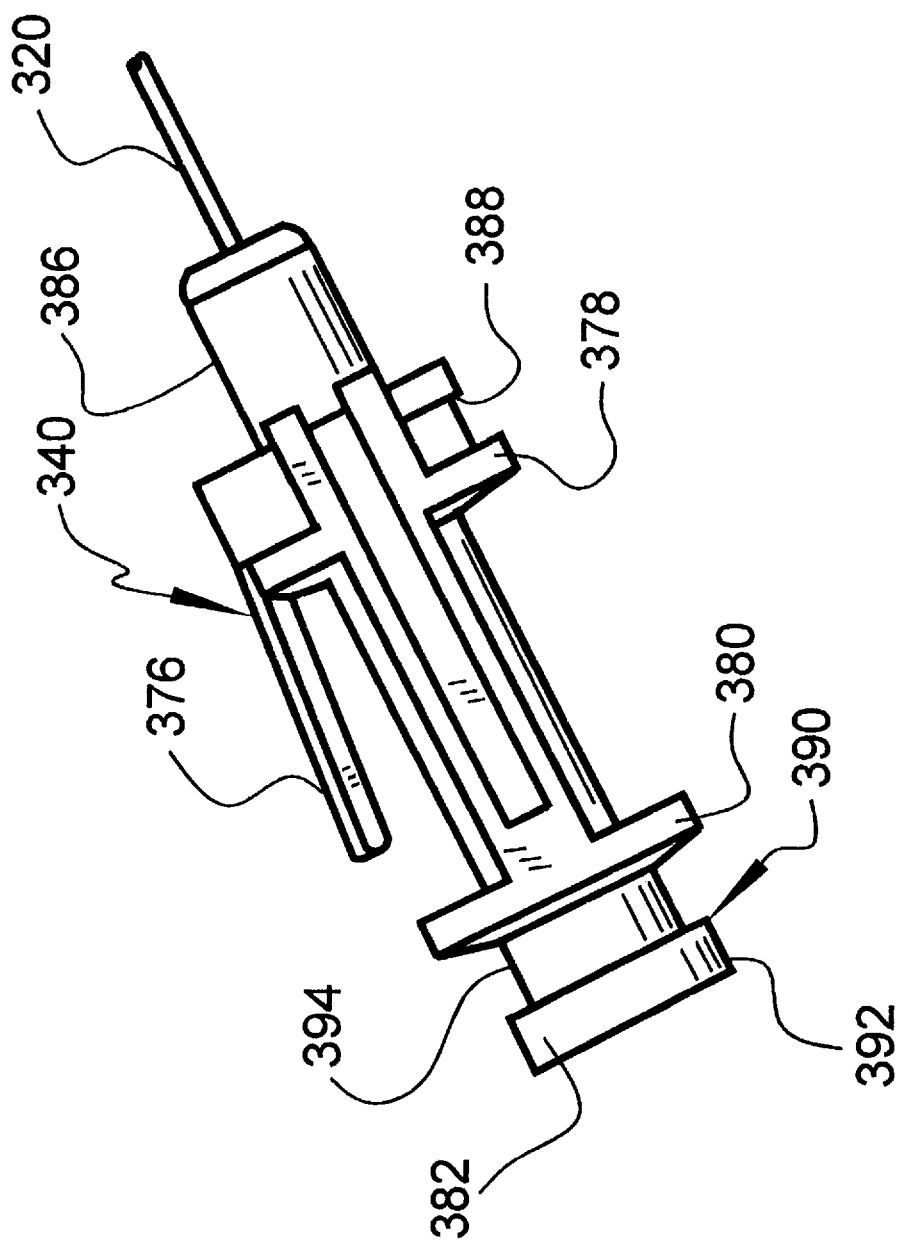
FIG. 32 is a perspective of a needle hub of the catheter apparatus seen in FIG. 29.

As seen in FIG. 32, hub 340 comprises a latch part 376, stabilizing disks 378 and 380 for lateral support of hub 340 within barrel 302 and a plunger attachment hub 382. Also hub 340 comprises a cylindrical hole 384 (see FIG. 29) sized to accept catheter needle 320 and a proximal hub 386 upon which IV catheter 310 is releasibly connected for transport and prior to separation from hub 386 after needle 320 retraction. Disposed immediately distal and inferiorly of hub 386 is an axially protruding catch 388, the purpose and function of which is disclosed hereafter.

Hub 382 also comprises a filter (not shown) which selectively passes gas, but which is impervious to liquids, and a pathway from needle 320 to the filter. Such filters are available from Paras Corporation. Additionally another pathway (also not shown) is provided from the filter to atmosphere such that air resident in needle 320 at the beginning of a procedure escapes through the filter and fluid is thereby permitted to flow to the filter through needle 320. Such fluid, when the catheter is placed into a patient's vessel provides a red "flash" signalling needle 320 entry into the vessel.

Hub 382 comprises an outer surface contour 390 comprising a raised plunger connecting part 392 and a depressed plunger anchoring part 394 for mooring plunger 351. Such connecting parts are well known in the art of manufacturing disposable syringes.

Figure 33:
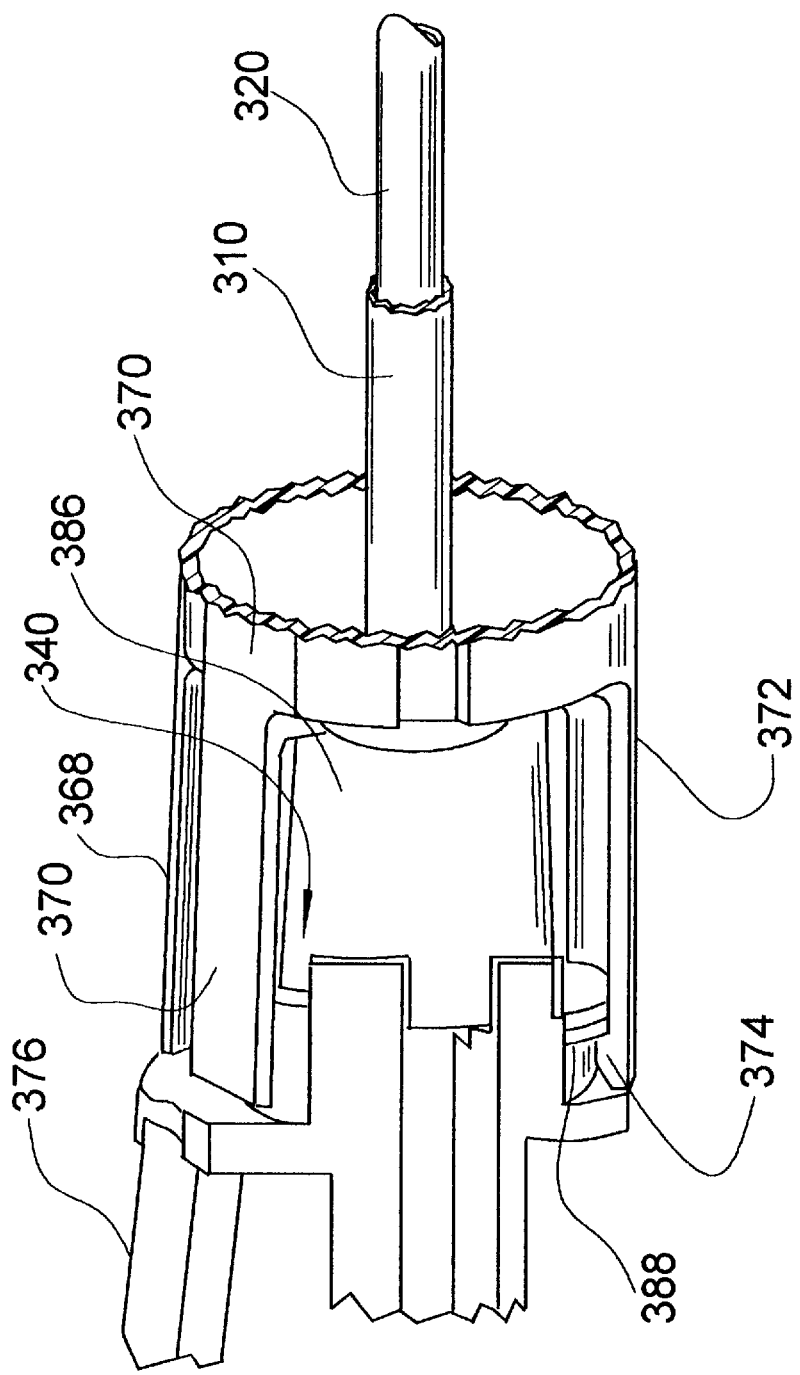
FIG. 33 is a perspective of a combination of sections of the cover of FIG. 31 and the hub of FIG. 32.

Reference is now made to FIG. 33 wherein an attachment is seen between hub 340 and a portion of cover 350. Note that legs 368, 370 and 372 are engaged about hub 386 and other portions of hub 340. Latch element 374 is selectively caught upon protruding catch 388 which causes cover 350 to be firmly affixed to hub 340 as long as latch element 374 (and associated leg 372 is confined within a catheter barrel 302. However, after latch element 374 is free of barrel 302, rotation of cover 350 frees latch element 374 from catch 388 permitting cover 350 to be removed from hub 340 and therefore from device 300.

Figure 34:
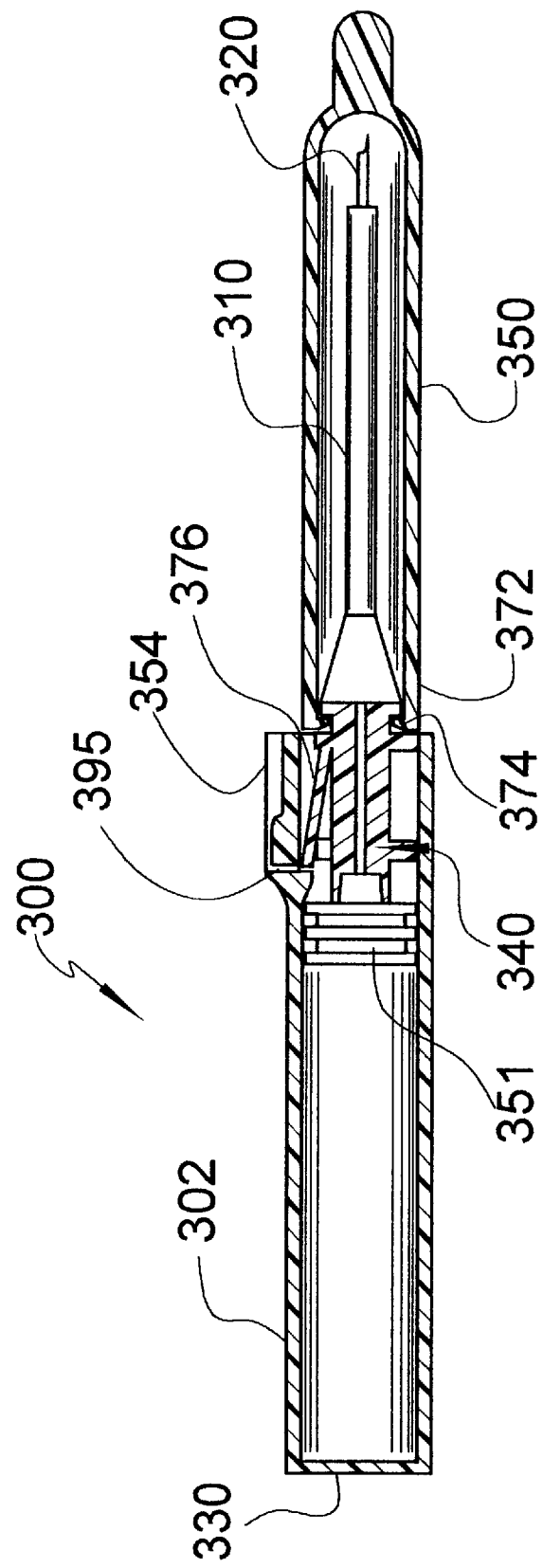
FIG. 34 is a cross section of the catheter apparatus of FIG. 29 comprising a needle, catheter and needle cover extended for use.

In FIG. 34, device 300 is seen with needle 320 and catheter extended. It is important to note that, as cover 350 is used to pull hub 340 outward from barrel 302 to extend needle 320 and catheter 310 for use in a medical procedure, a vacuum is pulled within barrel 302 by interaction of plunger 351, barrel 302 and barrel-end closing disk 330. When needle 320 and catheter 310 are adequately extended and before cover 350 is released latch 376 is caught upon a catch 395 disposed distal to button 354. To retract needle 320, cantilevered button 354 is depressed against latch 376 to free hub 350. Energy stored by the vacuum then resident in the volume defined by barrel 302, disk 330 and plunger 351 causes needle 320 to be moved distally from enclosure by catheter 310 and into safe containment of barrel 302.

Figure 35:
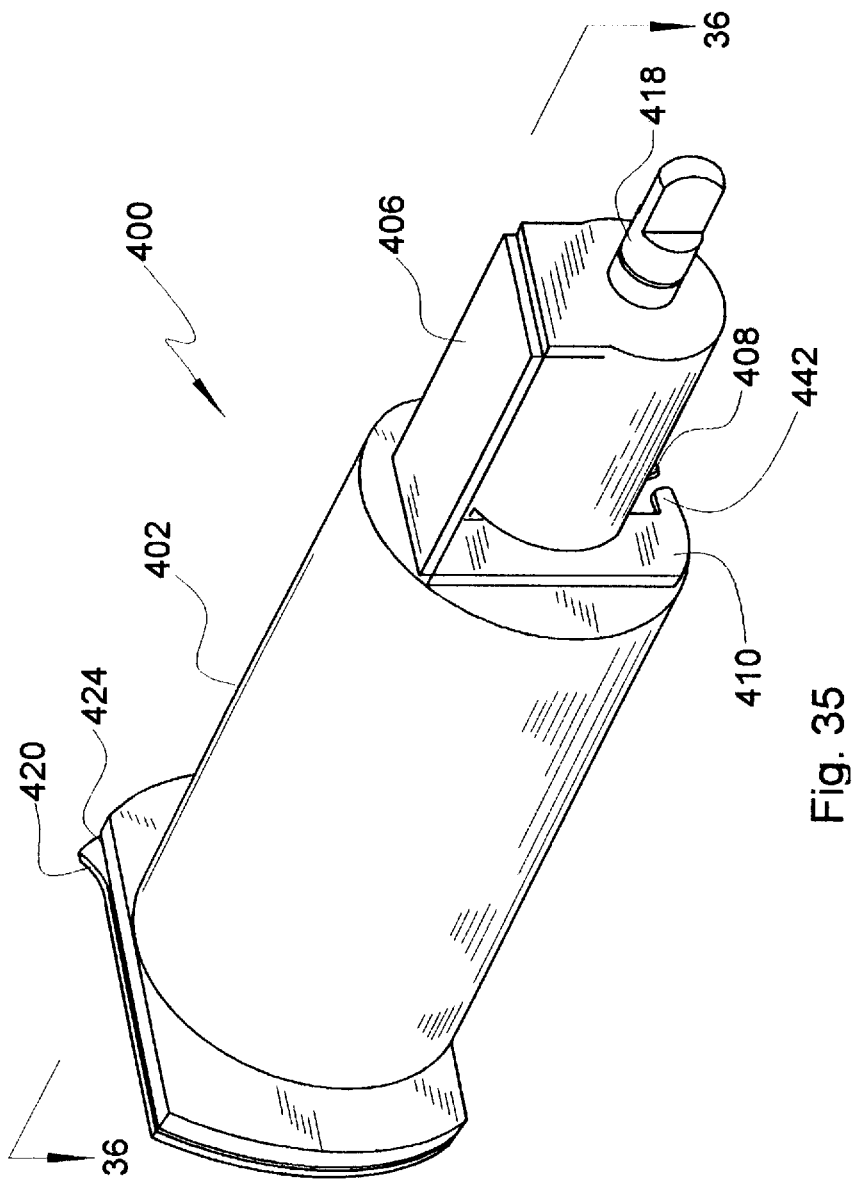
FIG. 35 is a perspective of a self contained medical phlebotomy needle device comprising a barrel and safety medical needle apparatus as an integral unit.
Figure 36:
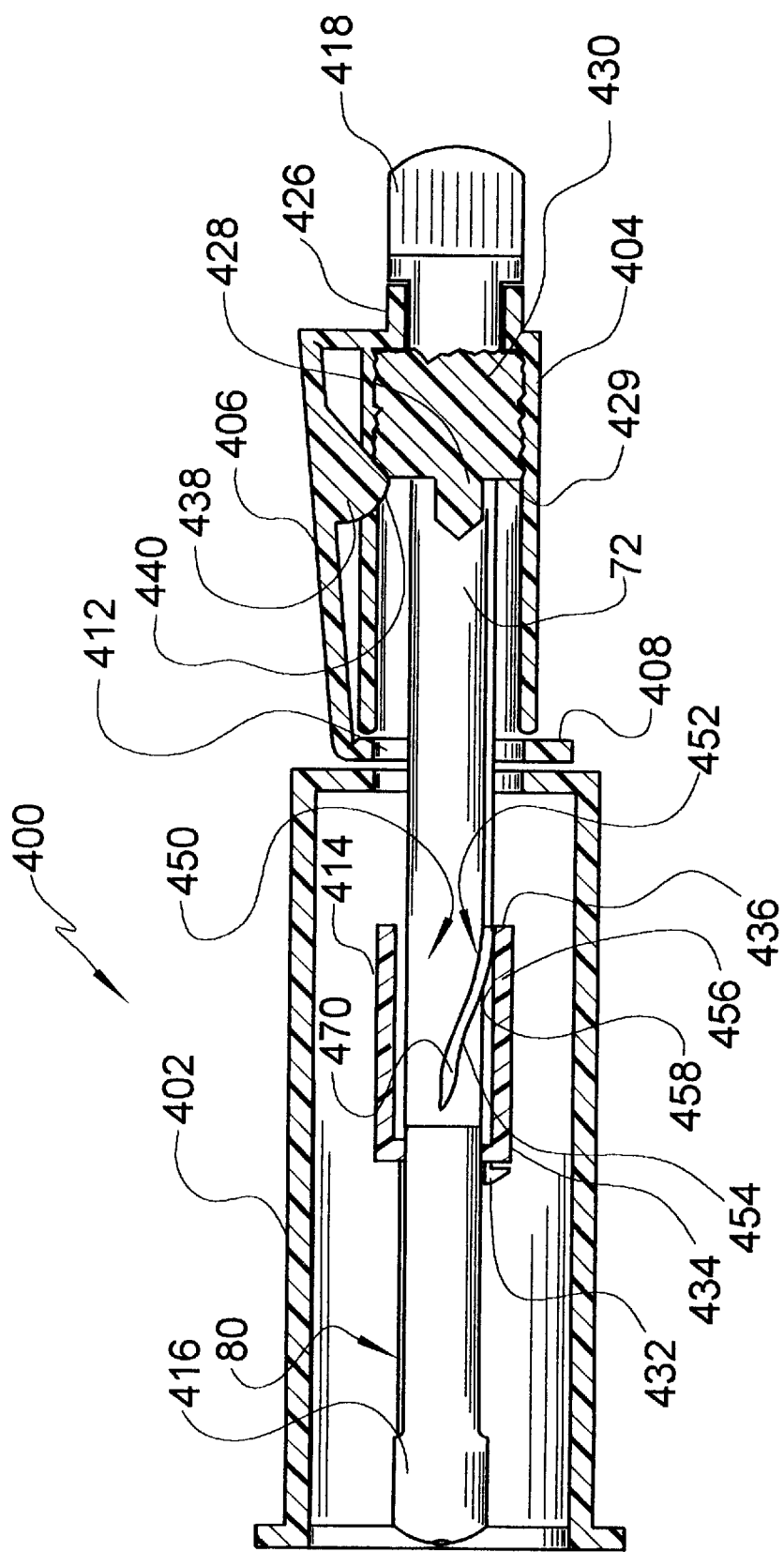
FIG. 36 is a cross section of the device of FIG. 35.

Another embodiment of a needle extension and retraction device 400 is seen in FIGS. 35 and 36. Device 400 comprises a barrel part 402, which is similar to barrel 202 (but does not contain optional slot 210), and a segment 404 which is similar to segment 204. Segment 402 also comprises a trigger strip 406, which is similar in function to strip 206, having a pair of legs 408 and 410 which are comparable to legs 226 and 228. Strip 206 also comprises a circular opening 412, similar to circular portion 224, which permits passage of a rear hub 414, in a manner in which rear hub 60 is permitted to pass through portion 224. However, in operation rear hub 414 traverses through opening 412 as a needle 70 is extended for use and then once more as needle 70 is retracted to safe containment. In FIGS. 35 and 36 device 400 is in a pre-use state. In FIG. 36, device 400 is seen to further comprise a sheath 416 (which is similar in form and function to sheath 90), a snubber 80, a tube 72, and a front cover 418 (which is similar in form and function to 50). It is consequential to note that, when design considerations for combined barrel 200 and assembly 10 and device 400 are appropriately met, three injection molded parts comprising the sheaths, the rear hubs, and the covers of combined barrel 200 and assembly 10 and device 400 may be the same parts. It is also important to note that the only other injection molded part of device 400 is barrel 402. Note also that a spring may be used in either assembly 10 or device 400 as the energy storing element. However, a spring is better used in device 400 because a retracted needle is fully covered by barrel parts 402 and 404.

The major differences between parts of assembly 10 and device 400 are found in barrel design. Barrel part 402 is designed to be an integral part and a part which is deposed with other parts of device 400. For that reason, it is desirable to add a removable label, such as label 420 seen in FIG. 35, to cover and protect distal opening 424 of barrel part 402 prior to use. Device 400 does not comprise a front hub. In place of the front hub is an integrally molded front or proximal part 426. Integrally molded hub 426 comprises an orifice for passage of needle 70, an insertion tab 428, seen as an internal section 430 of a segment 404 which seen in FIGS. 36 and 37 because an outer portion of segment 404 is removed for clarity of presentation and an annular stop 429.

To prepare device 400 for use in a medical procedure, cover 418 is pulled proximally. As seen in FIG. 36, cover 418 comprises a distally disposed release tab 432 which is inserted through a slot (not shown) in rear hub 414 and caught upon a distal face 434 of hub 414. Release tab 432 is designed be released by upward movement relative to hub 414. Thus, when cover 418 is pulled proximally, tube 72 is compressed, hub 414 is pulled by tab 432 and sheath 416 and snubber 80 are likewise brought forward within barrel part 402 and segment 404.

Three things occur as needle 70 and hub 414 are moved into position for use of device 400. In sequence, the following events prepare device 400 for use:

1. An annular, proximally facing surface 436 of hub 414 is drawn into contact with a tab 438. Tab 438 comprises a cam-shaped surface 440 which, in combination with a proximally moving hub 414, forces trigger strip 406 upward as hub 414 nears stop 429.

2. Once hub 414 has passed through opening 412, a lower segment of strip 406 comprising opening 412 and leg 410 is free to move upward. Leg 410 comprises an inwardly extending foot 442 (see FIG. 35) which is disposed to come into contact with tab 432 when hub 414 is disposed.

3. Continued upward movement of tab 432 discharges tab 432 from being latched upon surface 434 and cover 418 is thereby released to be withdrawn from device 400 to bare needle 70 for use.

Note that downward compression of strip 406 again places opening 412 in the pathway of hub 414 and results in retraction of needle 70 into safe containment. Note also that needle tip 140 should be retained in secure disposition proximal to a proximal face of molded hub 426 before use.

Note that a marked difference between rear hub 414 of device 400 and rear hub 60 of assembly 400 is a combination of a slot 450 and a latch arm 452, which are seen, at least in part in FIGS. 36 and 37. Latch arm 452 comprises an elongated arcuate extension 454 hinged to a side member 456 of hub 414 by a living hinge 458. Extension 454 comprises an outer surface 470 which has a contour which is essential the same as the outer surface of the rest of hub 414. As seen in FIG. 38, extension 454 comprises an inferiorly disposed bump 472. When extension 454 and therefore bump 472 are disposed medially as seen in FIG. 36, bump 472 acts as a stop or catch which impedes proximal movement of sheath 416 much as stop 180 impedes sheath 90, except, bump 472 is removed by causing extension 454 to swing laterally out of the way of sheath 416 when tab 428 is engaged with hub 414 as needle 70 is moved proximally by cover 418. As seen in FIG. 37, engagement of tab 428 with hub 414 (and extension 454) causes extension 454 to swing laterally about hinge 458. The lateral swing removes bump 472 from the path of sheath 416, permitting sheath 416 to move freely until hub 414 is disengaged from segment 404. Disengagement of hub 414 is actuated by depressing strip 406 against segment 404 which, in turn, moves opening 412 into alignment with hub 414 releasing energy stored in tub 72 to force hub 414 and associated parts distally toward and into barrel part 402.

A concern which must be addressed in any embodiment is that of assurance of true capture of needle 70 upon retraction. Examples of apparatus for impeding outward passage of needle tip 140 have been disclosed herebefore. Another example, seen in FIG. 39, is a section of a central portion of a forward hub (designated 500) showing an asymmetric tubing connection 502 embodiment which retards a retracted needle 70 from reentering a needle pathway orifice 504 in forward hub 500. In combination tube 72 and tubing connection 502 act to permit needle 70 to be retracted through orifice 504, but bias needle tip 140 into contact with an internal face 506 of hub 500 after needle tip 140 is fully retracted into hub 500. This is accomplished by providing a discontinuity 508 in the wall of tubing connection 502. Discontinuity 508 permits a section 510 of tube 72 to be distorted by needle 70 until needle 70 is retracted. However, after retraction, section 510 of tube 72 relaxes to a position indicated by dashed lines 512 and partially closes the needle reentry orifice. In this manner, needle tip 140 and needle 70 are securely trapped inside front hub 500. Not that the front plate which comprises internal face 506 must be puncture proof or at least puncture resistant to reasonable lateral forces placed upon needle 70 in the direction of face 506.

Figure 40:
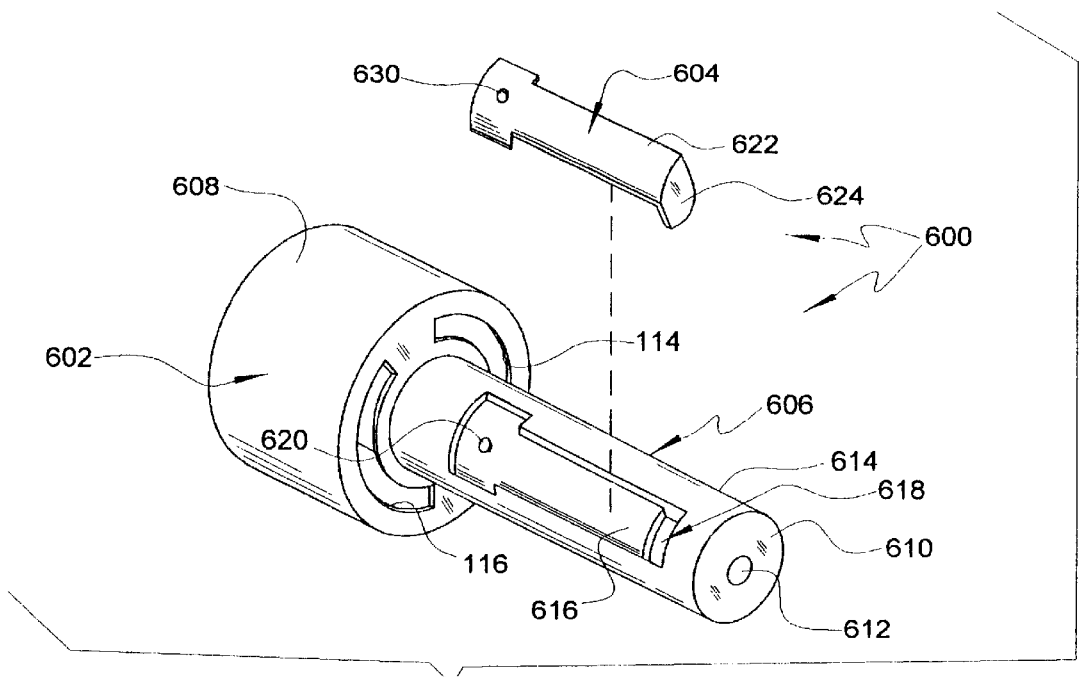
FIG. 40 is an exploded perspective of a forward needle hub assembly comprising a metal needle stop.
Figure 41:
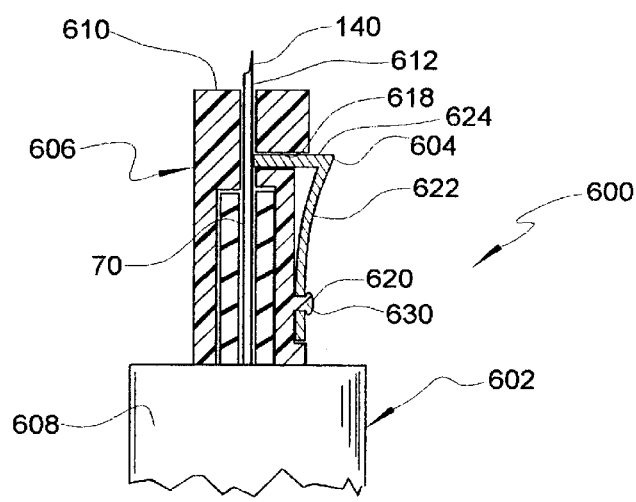
FIG. 41 is a side elevation of a portion of the forward needle hub assembly of FIG. 40 with an inserted needle, the stop assembled to the rest of the hub and proximal portions of the hub seen in cross section for better presentation of those parts of this forward needle hub compared to hub seen in earlier figures.

In those cases where a front plate or other needle tip 140 containing parts are made from material which is not puncture proof or even sufficiently puncture resistant, a needle impervious material should be used to effectively capture and hold needle tip 140 from exiting a forward hub, thereby creating an unsafe condition. Reference is made to FIGS. 40 and 41 wherein a forward hub assembly 600 is seen. Hub assembly 600 comprises a moldable part 602 (which may be made from a synthetic resinous material such as polypropylene) and a spring part 604. Other than structural differences which permit assembling part 604 to part 602, Forward hub assembly 600 is similar in form and function to forward hub 40 and other similar hubs disclosed herebefore.

Moldable hub part 602 comprises an elongated proximal cylindrical housing segment 606 and a pair of slots, 114 and 116, disposed in a cylindrical connector segment 608. Segment 606 comprises a forward blunt end 610 and an internal cylindrical needle passage 612. Inset within an external surface 614 is a depression 616. Depression 616 comprises a form and shape which comfortably accepts insertion of spring part 604. Disposed within depression 616 is a locking slot 618 and a raised mounting tab 620.

Spring part 604 is preferably made from spring steel, although any material which provides a safe barrier which prevents escape of needle tip 142 after needle 70 is retracted may be used. Spring part 604 comprises an elongated strip 622 and a stopping segment 624 which is essentially at a right angle to strip 622 to permit insertion of segment 624 through slot 618 and further insertion of segment 624 through slot 618 into a needle tip 140 obstructing position after needle 70 is retracted. In addition, an attachable support mount should be used to provide a secure attachment of spring part 604 to segment 606. As seen in FIGS. 40 and 41, spring part 604 comprises a mounting hole 630 which is securely affixed to tab 620, preferably by a press fit. Such connections are common in the assembly of plastic parts to other parts such as parts made from metal. Once spring part 604 is affixed to hub part 602, a combination of locking attachment of tab 620 about hole 630 and geometry of inset 616 relative to spring part 604 maintains structural integrity of assembly 600.

As seen in FIG. 41, when needle 170 is in a pre-use state with needle tip 140 disposed proximal to end 610, segment 624 rests upon needle 170 through slot 618. When needle tip 140 is retracted past slot 618 and segment 624 (not shown), spring tension retained in strip 622 discharges segment 624 further into needle passage 612 to from an effective and safe stop.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed and desired to be secured by Letters Patent is:

1. An extendable and retractable catheter needle assembly comprising:

a housing;

a catheter needle which is disposed within an IV catheter for a medical procedure comprising transcutaneous insertion of the catheter into a patient;

means for extending said catheter needle and catheter from the housing for use in the medical procedure, said extending means comprising:

a cover which provides protection for both needle and catheter and by which the needle is extended for use;

an energy storing means which stores energy as the catheter needle and catheter are extended;

latching means by which the catheter needle is latched in an extended state for use in a medical procedure;

said housing comprising a cantilevered button which is integral with said housing and which is depressed to release the latching means from the latched state, thereby causing the needle to be safely retracted into the housing.

2. An extendable and retractable catheter needle assembly according to claim 1 wherein said, in combination said housing, cover and latching means comprise a quick release such that the cover is released from further extending the needle when the cover is pulled out of the housing.

3. An extendable and retractable catheter needle assembly according to claim 1 wherein said energy storing means comprise means for pulling a vacuum which is acted upon by atmospheric pressure to provide retractable force for the needle.

* * * * *